US012800568B2

(12) United States Patent
Nakamura et al.

(10) Patent No.: US 12,800,568 B2
(45) Date of Patent: Nov. 17, 2026

(54) URINE SPECIMEN ANALYSIS METHOD AND URINE SPECIMEN ANALYZER

(71) Applicant: SYSMEX CORPORATION, Kobe (JP)

(72) Inventors: Yukiko Nakamura, Kobe (JP); Masanori Kawano, Kobe (JP); Kenta Hamasaki, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 868 days.

(21) Appl. No.: 18/169,983

(22) Filed: Feb. 16, 2023

(65) Prior Publication Data

US 2023/0266298 A1 Aug. 24, 2023

(30) Foreign Application Priority Data

Feb. 18, 2022 (JP) ................................ 2022-024062

(51) Int. Cl.
*G01N 15/14* (2024.01)
*G01N 15/1434* (2024.01)
*G01N 33/48* (2006.01)
*G01N 33/493* (2006.01)
*G01N 33/50* (2006.01)

(52) U.S. Cl.
CPC ....... *G01N 33/493* (2013.01); *G01N 33/5091* (2013.01)

(58) Field of Classification Search
None
See application file for complete search history.

(56) References Cited

U.S. PATENT DOCUMENTS

2015/0247802 A1* 9/2015 Ozasa ................ G01N 15/1429 435/6.15
2018/0017480 A1* 1/2018 Fukuda .................... G01N 1/14
2019/0147136 A1 5/2019 Lu et al.

FOREIGN PATENT DOCUMENTS

JP 2015049066 A 3/2015
JP 2015163855 A 9/2015
JP 2016512337 A 4/2016
JP 6116502 B2 4/2017

OTHER PUBLICATIONS

Tjagur et al. ("Profile of sexually transmitted infections causing urethritis and a related inflammatory reaction in urine among heterosexual males: A flow-cytometry study," Plos One, Dec. 2, 2020, pp. 1-15 (Year: 2020).*

(Continued)

*Primary Examiner* — Neil N Turk
(74) *Attorney, Agent, or Firm* — JCIPRNET

(57) ABSTRACT

Disclosed is a urine specimen analysis method for obtaining information about a urine particle in a urine specimen, and the urine specimen analysis method includes: obtaining count information about the number of *Trichomonas vaginalis* cells and first information including count information about at least one of the number of squamous epithelium cells and the number of white blood cells, based on detection data of the urine particle in the urine specimen; and outputting information about suspicion of *Trichomonas* infection based on at least the count information about the number of *Trichomonas vaginalis* cells, and the first information.

6 Claims, 16 Drawing Sheets

(56) References Cited

OTHER PUBLICATIONS

Delanghe et al., "The role of automated urine particle flow cytometry in clinical practice", Clinica Chimica Acta, Nov. 1, 2000, vol. 301, No. 1-2, pp. 1-18.

Nakayama et al., "Outline and Features of UF-5000, Fully Automated Urine Particle Analyzer", Sysmex Journal International, Jan. 1, 2018, vol. 28, No. 1, pp. 1-21.

Wang et al., "Increase Trichomonas vaginalis detection based on urine routine analysis through a machine learning approach", Scientific Reports, Aug. 19, 2019, vol. 9, No. 1, pp. 1-10.

Extended European Search Report issued Jun. 19, 2023, by the European Patent Office in corresponding European Patent Application No. 23156264.6. (10 pages).

* cited by examiner

TRICHOMONAS-POSITIVE SPECIMEN

[SF] DSSP × FSCP

TRICHOMONAS-POSITIVE SPECIMEN

[CR] SSHA × FSCW

TRICHOMONAS-NEGATIVE SPECIMEN

[SF] DSSP × FSCP

TRICHOMONAS-NEGATIVE SPECIMEN

[CR] SSHA × FSCW

FIG. 15

ANALYSIS MODE

| | | |
|---|---|---|
| FIRST MODE (STANDARD) | | |
| 75a | FIRST MEASUREMENT SAMPLE SF: Trich THRESHOLD VALUE (N1) | 1.0/uL |
| | SECOND MEASUREMENT SAMPLE CR: Trich THRESHOLD VALUE (N2) | 5.0/uL |
| | squa EC THRESHOLD VALUE (N3) | 5.0/uL |
| SECOND MODE (SENSITIVITY-ORIENTED) | | |
| 75b | FIRST MEASUREMENT SAMPLE SF: Trich THRESHOLD VALUE (N1) | 1.0/uL |
| | SECOND MEASUREMENT SAMPLE CR: Trich THRESHOLD VALUE (N2) | 1.0/uL |
| | squa EC THRESHOLD VALUE (N3) | 1.0/uL |
| THIRD MODE (SPECIFICITY-ORIENTED) | | |
| 75c | FIRST MEASUREMENT SAMPLE SF: Trich THRESHOLD VALUE (N1) | 10.0/uL |
| | SECOND MEASUREMENT SAMPLE CR: Trich THRESHOLD VALUE (N2) | 20.0/uL |
| | squa EC THRESHOLD VALUE (N3) | 20.0/uL |

FIG. 16

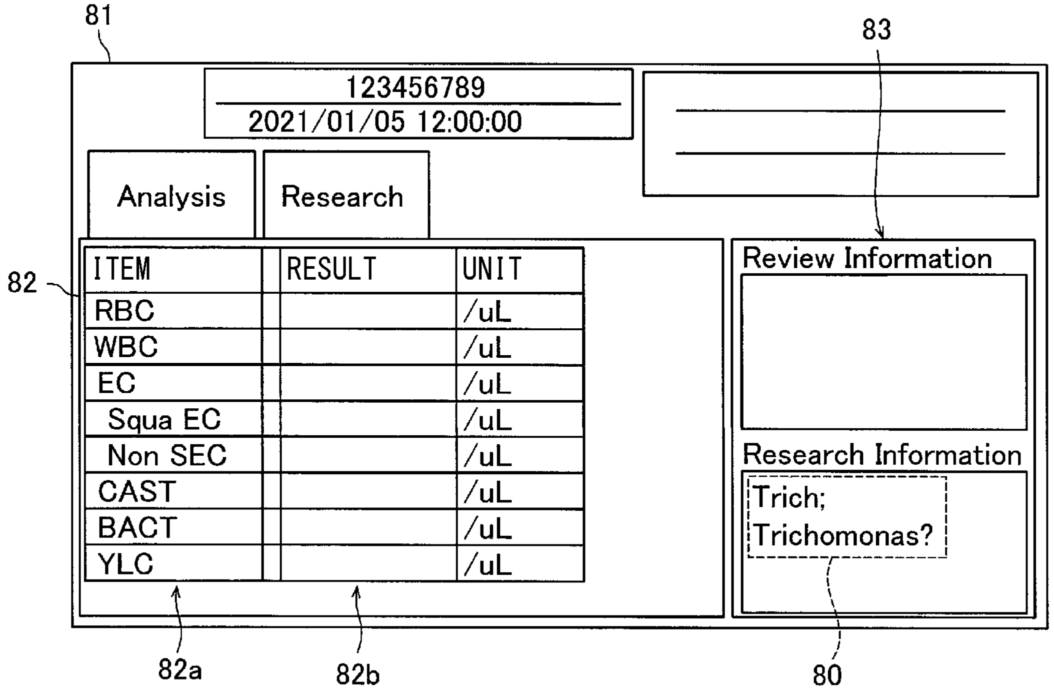

(FIRST EMBODIMENT)

DETERMINATION BASED ON COUNT INFORMATION OF TRICHOMONAS VAGINALIS, FIRST INFORMATION, AND SECOND INFORMATION (THIRD EMBODIMENT)

(FOURTH EMBODIMENT)

(DETERMINATION RULE 1A)

URINE SPECIMEN ANALYSIS METHOD AND URINE SPECIMEN ANALYZER

CROSS REFERENCE TO RELATED APPLICATIONS

This application claims priority from prior Japanese Patent Application No. 2022-024062, filed on Feb. 18, 2022, entitled "URINE SPECIMEN ANALYSIS METHOD AND URINE SPECIMEN ANALYZER", the entire content of which is incorporated herein by reference.

FIELD OF THE INVENTION

The present invention relates to a urine specimen analysis method and a urine specimen analyzer for obtaining information about a urine particle in a urine specimen.

BACKGROUND OF THE INVENTION

Japanese Laid-Open Patent Publication No. 2015-163855 discloses a urine specimen analyzer that obtains detection data of urine particles in a urine specimen through flow cytometry, and counts the urine particles for each kind based on the detection data. The urine specimen analyzer identifies *Trichomonas vaginalis* in the urine particles based on fluorescence intensity and forward scattered light intensity obtained for each urine particle as the detection data, and counts the identified *Trichomonas vaginalis* cells.

*Trichomonas vaginalis* is similar in form to another urine particle such as a white blood cell or a deep-layer squamous cell in urine. Therefore, there is a limitation in accuracy with which *Trichomonas vaginalis* is distinguished from other particles and counted.

SUMMARY OF THE INVENTION

The scope of the present invention is defined solely by the appended claims, and is not affected to any degree by the statements within this summary.

A urine specimen analysis method according to a first invention for attaining the aforementioned object is directed to a urine specimen analysis method for obtaining information about a urine particle in a urine specimen (5) (see FIG. 2), and the urine specimen analysis method includes: obtaining count information (70) about the number of *Trichomonas vaginalis* cells and first information (71) including count information about at least one of the number of squamous epithelium cells and the number of white blood cells, based on detection data of the urine particle in the urine specimen (5) (S5); and outputting information (80) (see FIG. 1) about suspicion of *Trichomonas* infection based on at least the count information (70) about the number of *Trichomonas vaginalis* cells, and the first information (71) (S7 and S8), as shown in FIG. 1, FIG. 13, and FIG. 17.

A urine specimen analyzer (100) according to a second invention includes: a detector (30) configured to detect a urine particle in a urine specimen (5) (see FIG. 2), and an analysis unit (20) configured to obtain count information (70) about the number of *Trichomonas vaginalis* cells and first information (71) including count information about at least one of the number of squamous epithelium cells and the number of white blood cells, based on detection data of the urine particle in the urine specimen (5), and output information (80) about suspicion of *Trichomonas* infection based on at least the count information (70) about the number of *Trichomonas vaginalis* cells, and the first information (71), as shown in FIG. 1, FIG. 13, and FIG. 17

BRIEF DESCRIPTION OF THE DRAWINGS

FIG. 15 illustrates a threshold value set for each mode for the analysis unit;

FIG. 16 illustrates an example of an analysis result screen;

DETAILED DESCRIPTION

First Embodiment

A first embodiment will be described below with reference to the drawings. Firstly, the entire configuration of a urine specimen analyzer 100 of the first embodiment will be described with reference to FIG. 1. The urine specimen analyzer 100 analyzes a urine particle in a urine specimen. Examples of the urine particle can include a red blood cell, a white blood cell, an epithelial cell, a cast, and bacteria. The urine specimen analyzer 100 is further configured to detect *Trichomonas vaginalis* as a urine particle and perform analysis for suspicion of *Trichomonas* infection.

(Entire Configuration of Urine Specimen Analyzer)

Figure 1:
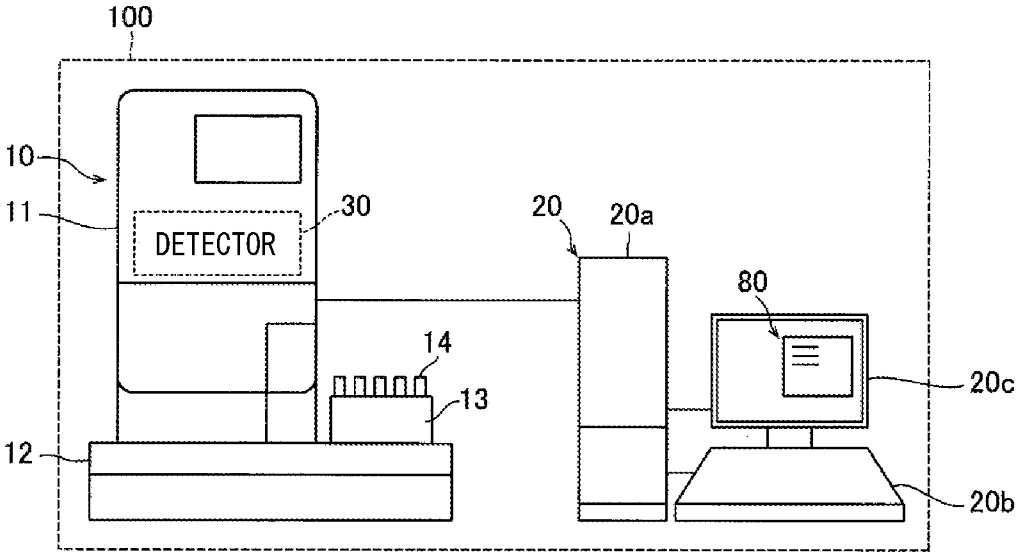
FIG. 1 is a schematic diagram illustrating an example of a configuration of a urine specimen analyzer.

As shown in FIG. 1, the urine specimen analyzer 100 includes at least a measurement unit 10 and an analysis unit 20 as main components. The measurement unit 10 includes a detector 30, and a mechanism for suctioning a urine specimen, preparing a measurement sample, and supplying the prepared measurement sample to the detector 30. The measurement unit 10 includes a body portion 11 in which the detector 30 is stored, and a specimen transportation unit 12 for transporting a specimen rack 13. The analysis unit 20 is disposed separately from the measurement unit 10, and is connected to the measurement unit 10 so as to enable data communication therewith.

The specimen rack 13 can hold a plurality of specimen containers 14 in an erected state such that openings of the specimen containers 14 face upward. The specimen container 14 stores a urine specimen 5 (see FIG. 2). The specimen container 14 is set at a predetermined feeding position in the specimen transportation unit 12 by a user in a state where the specimen container 14 is set in the specimen rack 13. The specimen transportation unit 12 is configured to transport the specimen container 14 held in the specimen rack 13 at the feeding position to a position at which the urine specimen 5 is suctioned by the measurement unit 10.

(Sample Preparation Unit)

Figure 2:
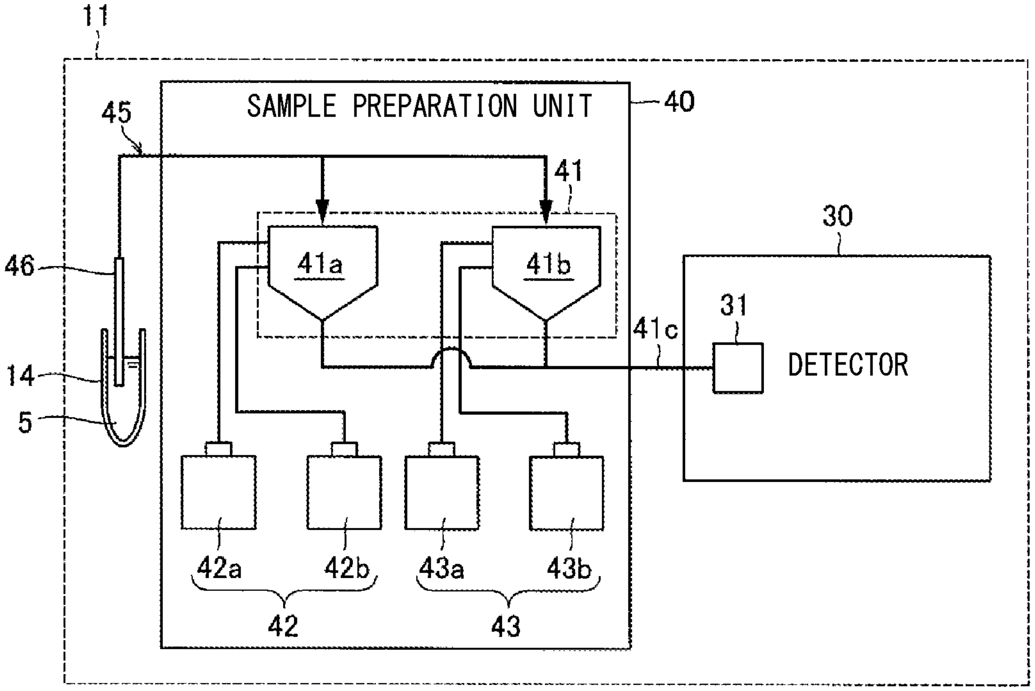
FIG. 2 is a block diagram illustrating an example of a configuration of a sample preparation unit.

As shown in FIG. 2, the body portion 11 of the measurement unit 10 includes a sample preparation unit 40 for preparing a measurement sample, and a specimen distributing unit 45 for supplying the urine specimen 5 to the sample preparation unit 40. The specimen distributing unit 45 suctions the urine specimen 5 in the specimen container 14 transported to the suctioning position, by a not-illustrated syringe pump, with use of a suction tube 46, and supplies the suctioned urine specimen 5 to the sample preparation unit 40.

The sample preparation unit 40 includes a mixing unit 41 for mixing the urine specimen 5 and a staining reagent. The mixing unit 41 is a reaction chamber having a predetermined volume. The urine specimen 5 and the staining reagent are mixed in the mixing unit 41, whereby a urine particle in the urine specimen 5 is stained with the staining reagent.

In the example shown in FIG. 2, the mixing unit 41 includes a first mixing unit 41*a* as a first reaction chamber for mixing the urine specimen 5 and a first reagent 42, and a second mixing unit 41*b* as a second reaction chamber for mixing the urine specimen 5 and a second reagent 43. The specimen distributing unit 45 distributes one part of the urine specimen 5 obtained from the specimen container 14 to the first mixing unit 41*a* and another part thereof to the second mixing unit 41*b*.

The first reagent 42 includes a first staining solution 42*a* and a first diluent 42*b*. A reagent container of the first staining solution 42*a* and a reagent container of the first diluent 42*b* are set in the sample preparation unit 40. The second reagent 43 includes a second staining solution 43*a* and a second diluent 43*b*. A reagent container of the second staining solution 43*a* and a reagent container of the second diluent 43*b* are set in the sample preparation unit 40.

The urine specimen 5 distributed to the first mixing unit 41*a* is mixed with the first reagent 42 (the first staining solution 42*a* and the first diluent 42*b*). The first reagent 42 stains an anucleate urine particle. The urine specimen 5 treated with the first reagent 42 in the first mixing unit 41*a* is used mainly for analyzing an anucleate particle such as a red blood cell and a cast. Hereinafter, the urine specimen 5 treated with the first reagent 42 in the first mixing unit 41*a* is referred to as a first measurement sample.

The urine specimen 5 distributed to the second mixing unit 41*b* is mixed with the second reagent 43 (the second staining solution 43*a* and the second diluent 43*b*). The second reagent 43 lyses red blood cells and crystals in the urine specimen 5, and stains nucleic acid. The urine specimen 5 treated with the second reagent 43 in the second mixing unit 41*b* is used mainly for analyzing a nucleate cell such as a white blood cell, an epithelial cell, bacteria, and fungi. Hereinafter, the urine specimen 5 treated with the second reagent 43 in the second mixing unit 41*b* is referred to as a second measurement sample.

The first mixing unit 41*a* and the second mixing unit 41*b* are each connected to a flow cell 31 of the detector 30 via a liquid sending tube 41*c*. The sample preparation unit 40 supplies the first measurement sample in the first mixing unit 41*a* and the second measurement sample in the second mixing unit 41*b* separately to the flow cell 31 during measurement.

The first staining solution 42*a* contains a fluorescent dye for staining a urine particle having no nucleic acid.

The first diluent 42*b* is a reagent that contains a buffer as a main component. The first diluent 42*b* contains an osmotic pressure compensation agent so as to obtain a stable fluorescence signal without hemolyzing red blood cells.

The second staining solution 43*a* contains a dye for staining nucleic acid. The second staining solution 43*a* contains an intercalator for specifically staining nucleic acid or a fluorescent dye that binds to a minor groove. Examples of the intercalator include known cyanine-based, acridine-based, and phenanthridium-based dyes. Examples of the cyanine-based intercalator include SYBR Green I (SYBR is a registered trademark) and Thiazole orange. Examples of the acridine-based intercalator include Acridin orange. Examples of the phenanthridium-based intercalator include propidium Iodide and Ethidium bromide. Examples of the dye that binds to a minor groove include known dyes such as DAPI and Hoechst (registered trademark). Examples of the Hoechst dye that binds to a minor groove include Hoechst 33342 and Hoechst 33258. In the first embodiment, the cyanine-based intercalator is preferable, and SYBR Green I and Thiazole orange are particularly preferable.

The second diluent 43*b* contains a hemolytic agent. The second diluent 43*b* damages cell membranes to promote passing of the second staining solution 43*a* through membranes, and contains a cationic surfactant for hemolyzing red blood cells and contracting contaminants such as fragments of red blood cells. The kind of the surfactant is not limited to cationic surfactants and may be a nonionic surfactant.

The detector 30 detects each of a urine particle in the urine specimen 5 having the first reagent 42 mixed therein, and a urine particle in the urine specimen 5 having the second reagent 43 mixed therein. *Trichomonas vaginalis* can be detected as a signal that can be distinguished from other urine particles by both the measurement using the first measurement sample and the measurement using the second measurement sample.

(Detector)

Figure 3:
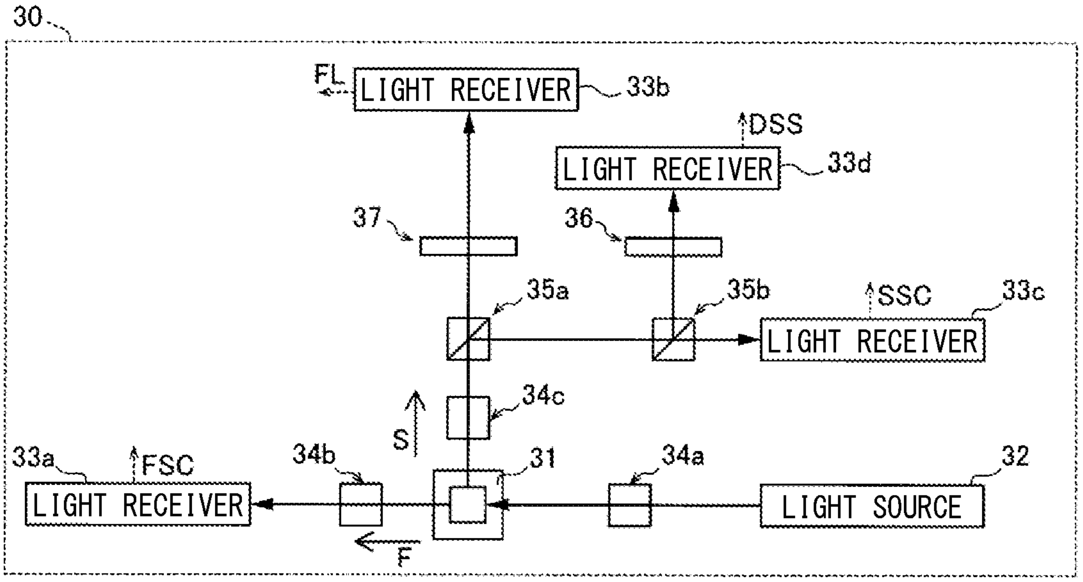
FIG. 3 is a block diagram illustrating an example of a configuration of a detector.

FIG. 3 illustrates main units of the detector 30 in a simplified manner. FIG. 3 is a plan view schematically showing a configuration of the detector 30. A measurement sample flows from the lower side toward the upper side along an axis perpendicular to the surface of the drawing sheet in the flow cell 31. The detector 30 includes the flow cell 31 through which the urine specimen 5 flows, a light source 32 that applies light to the flow cell 31, and light receivers (33*a* to 33*d*) for receiving light from the flow cell 31. That is, the detector 30 is a flow cytometer for individually detecting a urine particle in the urine specimen 5 by flow cytometry. The flow cytometer allows detection of a large amount of urine particles in a short time period, and is thus suitable for detecting a small amount of urine particles in a large amount of urine particles. The number of *Trichomonas vaginalis* cells contained in urine is limited at the early stage of infection. Therefore, the flow cytometer is particularly advantageous in that early determination as to suspicion of *Trichomonas* infection can be performed even at the early stage of infection.

The light receivers (33*a* to 33*d*) receive fluorescence and scattered light from a urine particle. Thus, a plurality of kinds of reception light signals based on which various kinds of urine particles including *Trichomonas vaginalis* are identified can be obtained. As a result, a reception light signal suitable for identifying a urine particle can be selected from the plurality of kinds of reception light signals and used, whereby accuracy for identifying a urine particle can be enhanced. Furthermore, the detector 30 includes lenses 34*a*, 34*b*, 34*c*, mirrors 35*a*, 35*b*, a polarizing filter 36, and a spectral filter 37.

The first and the second measurement samples sent to the detector 30 each form a narrow flow surrounded by sheath liquid in the flow cell 31. Laser light is applied to the flow of the sample from the light source 32. Such an operation is automatically performed by operating, for example, not-illustrated pump and solenoid valve, through control of a microcomputer 51 (control unit) described below.

The light source 32 is a semiconductor laser light source that outputs laser light having a center wavelength of 488 nm. The lens 34*a* condenses the laser light emitted from the light source 32 onto the flow of the sample in the flow cell 31. The lens 34*a* forms a beam spot on the flow of the sample in the flow cell 31. By applying the laser light to a particle (urine particle) in the flow of the sample, forward scattered light is generated on the front side (F direction) of the flow cell 31, and side scattered light and side fluorescence are generated on the side (S direction) of the flow cell 31.

The lens 34*b* condenses the forward scattered light emitted from the urine particle in the measurement sample onto the light receiver 33*a*. The light receiver 33*a* is, for example, implemented by a photodiode. The lens 34*c* condenses the side scattered light and the side fluorescence emitted from the urine particle onto the mirror 35*a*. The mirror 35*a* is a dichroic mirror that reflects the side scattered light toward the mirror 35*b*, and allows the side fluorescence to be transmitted therethrough to the spectral filter 37. The side fluorescence transmitted through the spectral filter 37 is received by the light receiver 33*b* that is a photomultiplier. The mirror 35*b* is a half mirror that divides the side scattered light from the minor 35*a* into two, and allows the light to be transmitted therethrough to the light receiver 33*c* that is a photomultiplier, and reflects the light toward the polarizing filter 36. The side scattered light transmitted through the minor 35*b* is received by the light receiver 33*c*. The side scattered light transmitted through the polarizing filter 36 is received by the light receiver 33*d* that is a photomultiplier. The polarizing filter 36 transmits therethrough only side scattered light in which the polarization plane has been changed in a specific direction from a polarization state of laser light applied to the flow of the sample.

The light receiver 33*a*, the light receiver 33*b*, the light receiver 33*c*, and the light receiver 33*d* convert the received light signals to electric signals, to output a forward scattered light signal (hereinafter, referred to as "FSC"), a fluorescence signal (hereinafter, referred to as "FL"), a side scattered light signal (hereinafter, referred to as "SSC"), and a depolarization side scattered light signal (hereinafter, referred to as "DSS"), respectively. The light receiver 33*b* that generates the fluorescence signal (FL) can change sensitivity with respect to incident light by switching a drive voltage. The light receiver 33*b* selectively performs a normal sensitivity operation or a high sensitivity operation for detecting bacteria through control of the microcomputer 51 described below.

(Configuration for Controlling Measurement Unit)

Figure 4:
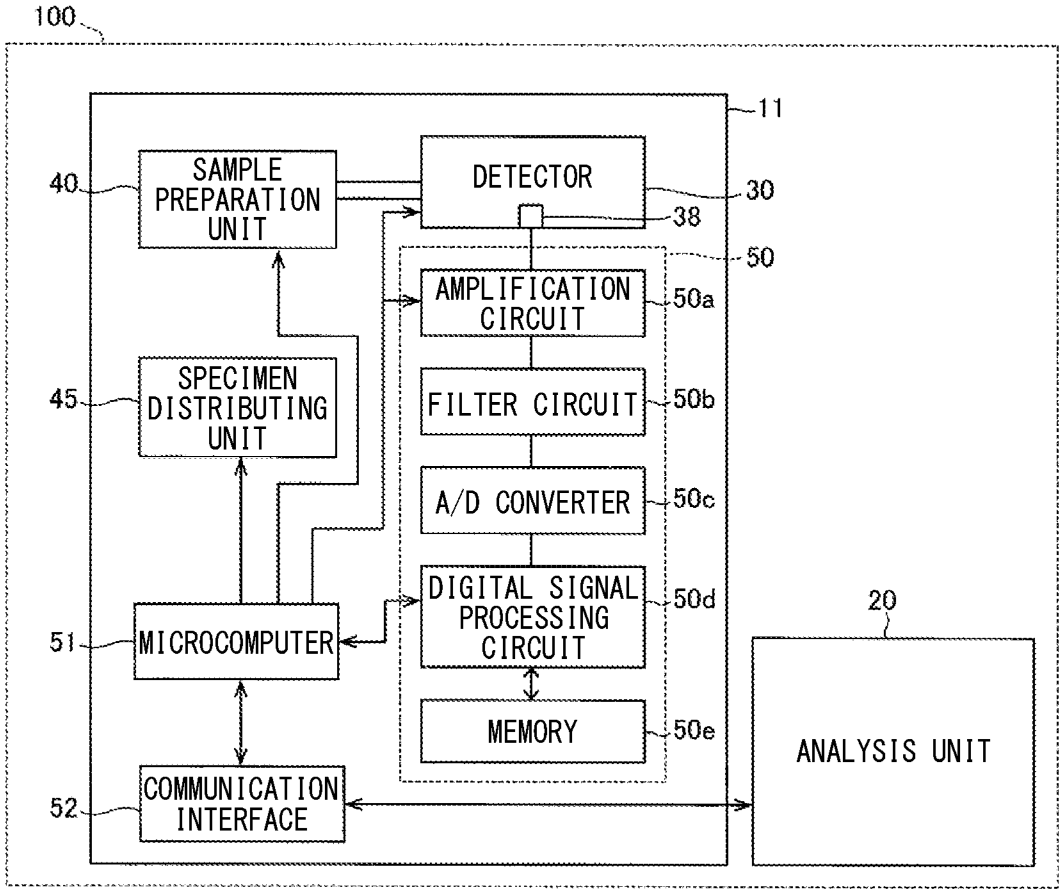
FIG. 4 is a block diagram illustrating a configuration for control of a measurement unit.

As shown in FIG. 4, the body portion 11 of the measurement unit 10 includes a signal processing circuit unit 50 for processing an output signal of the detector 30, the microcomputer 51, and a communication interface 52.

The signal processing circuit unit 50 includes an amplification circuit 50*a* for amplifying an output signal of the detector 30, a filter circuit 50*b* for performing a filtering process for an output signal of the amplification circuit 50*a*, an A/D converter 50*c* for converting an output signal (analog signal) of the filter circuit 50*b* to a digital signal, a digital signal processing circuit 50*d* for performing predetermined waveform processing for the digital signal, and a memory 50*e* connected to the digital signal processing circuit 50*d*.

The detector 30 amplifies each of FSC, SSC, FL, and DSS signals by a preamplifier 38. Each of the amplified signals is inputted to the amplification circuit 50*a*. The amplification circuit 50*a* amplifies four kinds of signals, that is, the FSC, SSC, FLH, and FLL signals, according to a gain having been set. For the amplification circuit 50*a*, a plurality of different gains can be set through control of the microcomputer 51.

The amplification circuit 50*a* amplifies a fluorescence signal (FL) obtained in the normal sensitivity operation at two kinds of amplification factors that are a high amplification factor and a low amplification factor. Therefore, a fluorescence signal (hereinafter, referred to as "FLH") obtained by amplification at the high amplification factor and a fluorescence signal (hereinafter, referred to as "FLL") obtained by amplification at the low amplification factor are obtained from a fluorescence signal (FL) corresponding to one particle. Furthermore, the amplification circuit 50*a* amplifies a fluorescence signal (FL) obtained in the high sensitivity operation for detecting bacteria at an amplification factor equal to the above-described high amplification factor. Hereinafter, the resultant fluorescence signal obtained at the high sensitivity and the high amplification factor is referred to as "FLH(B)". A setting value of the high sensitivity for detecting bacteria is five times the setting value of the normal sensitivity. Therefore, the FLH(B) corresponds to a signal obtained by amplification at an amplification factor that is five times that of the FLH.

The amplification circuit 50*a* amplifies a side scattered light signal (SSC) at two kinds of amplification factors that are a high amplification factor and a low amplification factor. Therefore, a side scattered light signal (high sensitivity) (hereinafter, referred to as "SSH") obtained by amplification at the high amplification factor and a side scattered light signal (low sensitivity) (hereinafter, referred to as "SSL") obtained by amplification at the low amplification factor are obtained from a side scattered light signal (SSC) corresponding to one particle.

The microcomputer 51 is connected to the sample preparation unit 40, the specimen distributing unit 45, the detector 30, the amplification circuit 50*a*, the digital signal processing circuit 50*d*, and the communication interface 52. The microcomputer 51 controls the specimen distributing unit 45, the sample preparation unit 40, the amplification circuit 50*a*, and the digital signal processing circuit 50*d* to measure a measurement sample and generate detection data. The communication interface 52 is connected to the analysis unit 20 via a LAN cable so as to be able to communicate with the analysis unit 20. The microcomputer 51 operates to transmit the detection data to the analysis unit 20 via the communication interface 52.

(Analysis Unit)

Figure 5:
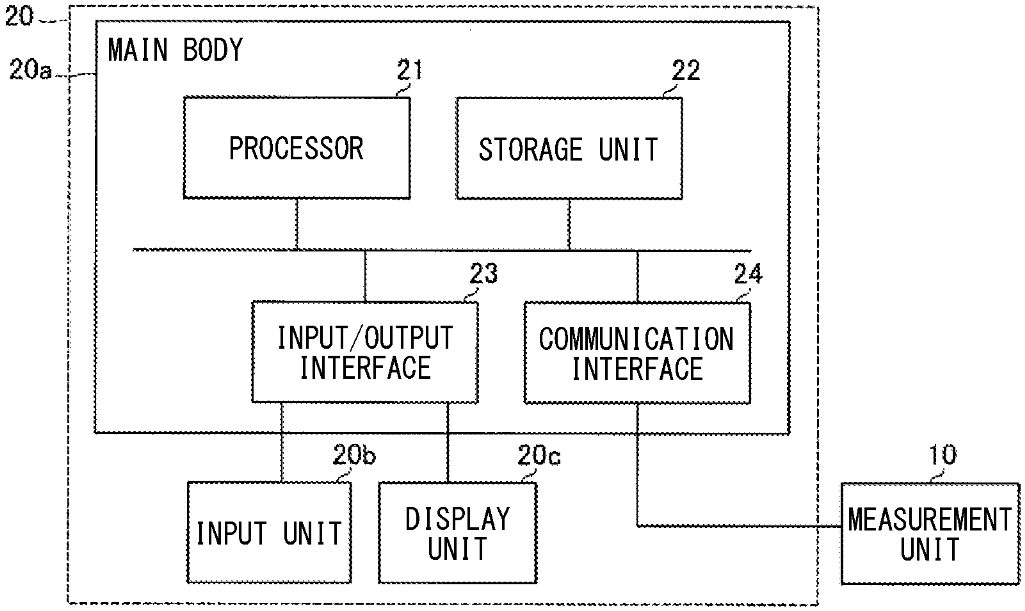
FIG. 5 is a block diagram illustrating an example of a configuration of an analysis unit.

As shown in FIG. 5, the analysis unit 20 is implemented by a personal computer. The analysis unit 20 includes a main body 20*a*, an input unit 20*b*, and a display unit 20*c*. The main body 20*a* includes a processor 21 implemented by a CPU, a storage unit 22, an input/output interface 23, and a communication interface 24.

The processor 21 executes a computer program stored in a ROM and a computer program loaded to a RAM. The storage unit 22 includes a ROM and a hard disk for storing the computer program, and is used as a work region for the processor 21 when the processor 21 executes the computer program stored in the hard disk.

In the storage unit 22, various computer programs such as an operating system and application programs to be executed by the processor 21, and data used for executing the computer programs are installed. In the storage unit 22, a computer program for analyzing detection data obtained from the measurement unit 10, and outputting an analysis result is installed. The computer program may be downloaded via a network or installed to the storage unit 22 from a storage medium such as an optical disc or a flash memory.

To the input/output interface 23, the input unit 20*b* including a mouse and a keyboard is connected. A user uses the input unit 20*b* to operate the analysis unit 20 and input data to the analysis unit 20. The input/output interface 23 is connected to the display unit 20*c* including a liquid crystal display, and outputs a video image signal corresponding to image data to the display unit 20*c*. The display unit 20*c* displays an image based on the inputted video image signal. The analysis unit 20 is connected to the communication interface 52 (see FIG. 4) of the measurement unit 10 via the communication interface 24. The processor 21 can perform transmission/reception of various data including detection data to/from the measurement unit 10 via the communication interface 24.

(Analysis Performed by Analysis Unit)

The analysis unit 20 analyzes a urine particle based on the detection data obtained from the measurement unit 10. The detection data generated by the measurement unit 10 includes FSC, SSH, SSL, FLH, FLL, FLH(B), and DSS signals that are detected from each urine particle contained in the measurement sample. The detection data generated by the measurement unit 10 includes detection data (hereinafter, referred to as "detection data (SF)") obtained from the first measurement sample and detection data (hereinafter, referred to as "detection data (CR)") obtained from the second measurement sample.

The analysis unit 20 extracts a plurality of feature parameters representing features of urine particles in the urine specimen 5, based on the detection data, and obtains count information for each kind of urine particle, based on the plurality of feature parameters having been extracted. Thus, appropriate feature parameters corresponding to the features of the respective kinds of the urine particles are combined, whereby accuracy for identifying a urine particle for each kind can be effectively enhanced. The count information of the urine particle specifically represents the number of detected urine particles. The number of the detected urine particles is referred to as "count value".

The feature parameter is defined by a combination of a kind of a detection signal, a kind of a feature quantity obtained from the detection signal, and a kind of detection data.

The kind of the detection signal conceptually represents any of the FSC, SSH, SSL, FLH, FLH(B), FLL, and DSS signals. The kind of the feature quantity obtained from the detection signal includes three kinds of quantities that are "peak intensity" shown in FIG. 6A, "pulse width" shown in FIG. 6B, and "pulse area" shown in FIG. 6C. Hereinafter, the peak intensity is represented as "P", the pulse width is represented as "W", and the pulse area is represented as "A". Hereinafter, the feature parameter is expressed by sequentially describing the kind of the detection signal and the kind of the feature quantity, and is, for example, expressed in the form of FSCP (peak intensity of forward scattered light signal), SSHW (pulse width of side scattered light signal (high sensitivity)), and FLLA (pulse area of low sensitivity side fluorescence signal).

Figure 6A:
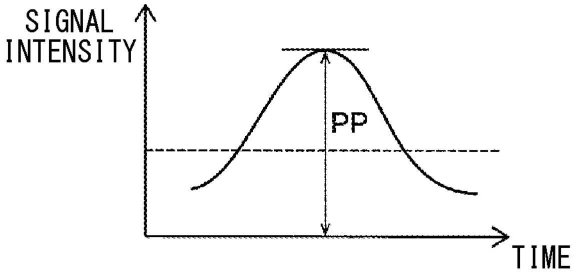
FIG. 6A shows a graph of a peak intensity as an example of a feature quantity of a detected signal.
Figure 6B:
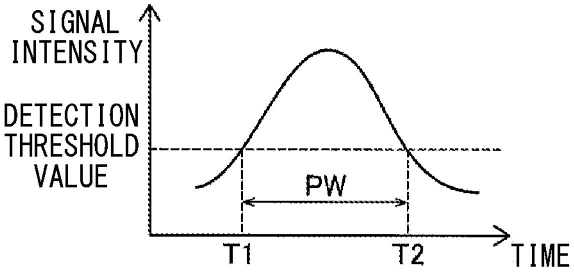
FIG. 6B shows a graph of a pulse width as an example of a feature quantity of a detected signal.
Figure 6C:
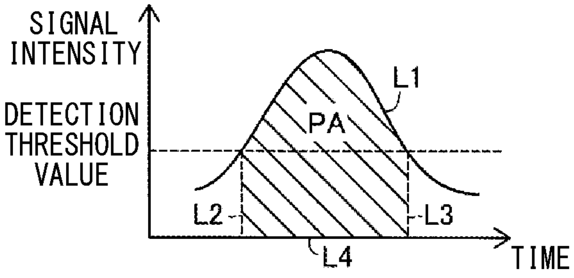
FIG. 6C shows a graph of a pulse area as an example of a feature quantity of a detected signal.

A urine particle in the flow of the sample passing through the flow cell 31 passes through a beam spot, whereby the detection signal of the detector 30 is generated. Therefore, as shown in FIGS. 6A to 6C, the detection signal has a pulse-shaped signal waveform. In the graphs in FIGS. 6A to 6C, the vertical axis represents signal intensities, and the horizontal axis represents time. As shown in FIG. 6A, the peak intensity "P" of each optical signal is obtained as a peak height PP of the pulse. The pulse width "W" of each optical signal is obtained as an interval PW from a time T1 at which the pulse exceeds a predetermined detection threshold value to a time T2 at which the pulse becomes lower than the detection threshold value, as shown in FIG. 6B. The pulse area "A" of each optical signal is obtained as an area of a region (hatched region) PA surrounded by a signal pulse waveform line L1, straight lines L2 and L3 each representing a time at which the pulse height takes a predetermined detection threshold value, and a straight line L4 at which the value of the optical signal intensity indicates 0, that is, obtained as a time integration value of the signal intensity, as shown in FIG. 6C. A feature quantity (for example, peak kurtosis, aspect ratio, differential value (gradient of waveform line)) other than the above-described peak intensity, pulse width, and pulse area may be obtained.

In a case where the number of kinds of the optical signals is seven, that is, the optical signals are FSC, SSH, SSL, FLH, FLL, FLH(B), and DSS, and the number of kinds of the feature quantities is three, that is, the feature quantities are the peak intensity P, the pulse width W, and the pulse area A, the number of combinations for the feature parameter can be 21. The detection data includes two kinds of detection data, that is, the detection data (SF) of the first measurement sample and the detection data (CR) of the second measurement sample. Therefore, among 42 combinations in total, the feature parameter having a combination suitable for distinguishing one kind of urine particle from the other urine particles is preset as the feature parameter for each kind of the urine particle.

The analysis unit 20 combines two or more feature parameters and identifies a kind of urine particle in the urine specimen 5 according to the detection data, and calculates the number of urine particles for each kind and thus generates the count information (count value) for each urine particle. The analysis unit 20 identifies a kind of urine particle, based on distribution data (see FIG. 7, FIG. 8) obtained by combining two or more feature parameters. The distribution data is obtained by plotting each urine particle, as coordinates corresponding to the feature parameters, in a scattergram in which each of the feature parameters is the axis for the coordinates.

<Specific Example of Feature Parameter>

Examples of a combination of the feature parameters used for identifying a urine particle which is particularly concerned with analysis for suspicion of *Trichomonas* infection, among the urine particles that can be detected by the urine specimen analyzer 100, will be described below.

<Red Blood Cell (RBC): SF_DSSP×FSCP>

Figure 7A:
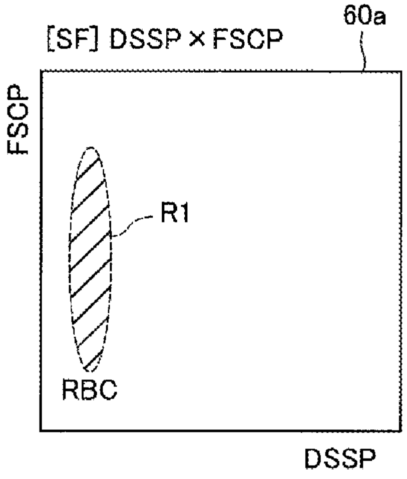
FIG. 7A illustrates distribution data representing a distribution region of red blood cells.

A red blood cell (RBC) is a urine particle appearing in a region R1 in distribution data 60*a* of the peak intensity (DSSP) of the depolarization side scattered light signal, and the peak intensity (FSCP) of the forward scattered light signal, in the detection data (SF) of the first measurement sample, as shown in FIG. 7A. Particles plotted in the region R1 are counted as red blood cells.

<White Blood Cell (WBC): CR_FLLA×FSCW>

Figure 7B:
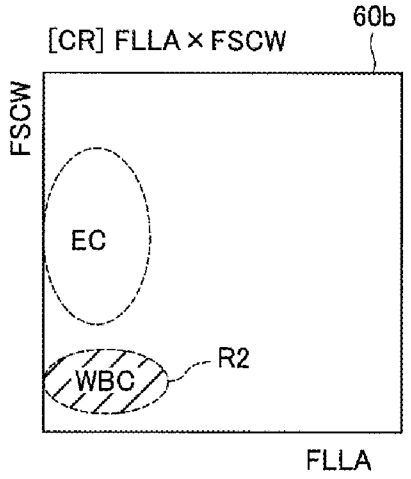
FIG. 7B illustrates distribution data representing a distribution region of white blood cells.

A white blood cell (WBC) is a urine particle appearing in a region R2 in distribution data 60*b* of the pulse area (FLLA) of the side fluorescence signal at the normal sensitivity and the low amplification factor, and the pulse width (FSCW) of the forward scattered light signal, in the detection data (CR) of the second measurement sample, as shown in FIG. 7B. Particles plotted in the region R2 are counted as white blood cells.

<Squamous Epithelium Cell (squaEC): CR_SSHA×FSCW>

Figure 7C:
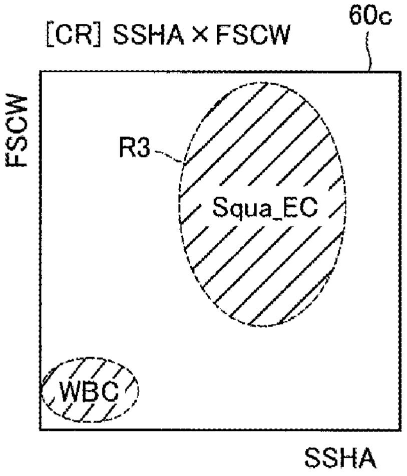
FIG. 7C illustrates distribution data representing a distribution region of squamous epithelium cells.

A squamous epithelium cell (squaEC) is a urine particle appearing in a region R3 in distribution data 60*c* of the pulse area (SSHA) of the side scattered light signal at the high amplification factor, and the pulse width (FSCW) of the forward scattered light signal, in the detection data (CR) of the second measurement sample, as shown in FIG. 7C. Particles plotted in the region R3 are counted as squamous epithelium cells.

<Bacteria (BACT): CR_FLH(B)P×FSCP>

Figure 7D:
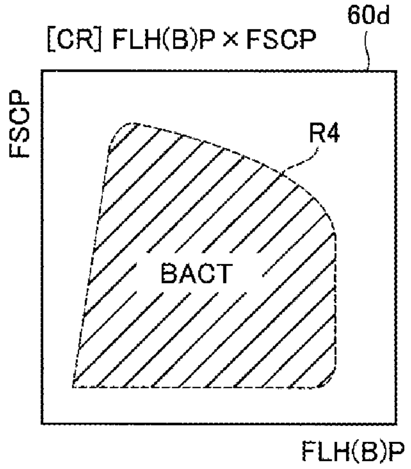
FIG. 7D illustrates distribution data representing a distribution region of bacteria.

Bacteria (BACT) are urine particles appearing in a region R4 in distribution data 60*d* of the peak intensity (FLH(B)P) of the side fluorescence signal at the high sensitivity for detecting bacteria and the high amplification factor, and the peak intensity (FSCP) of the forward scattered light signal, in the detection data (CR) of the second measurement sample, as shown in FIG. 7D. Particles plotted in the region R4 are counted as bacteria.

<Yeast-Like Fungi (YLC): CR_FLHP×FSCP>

Figure 7E:
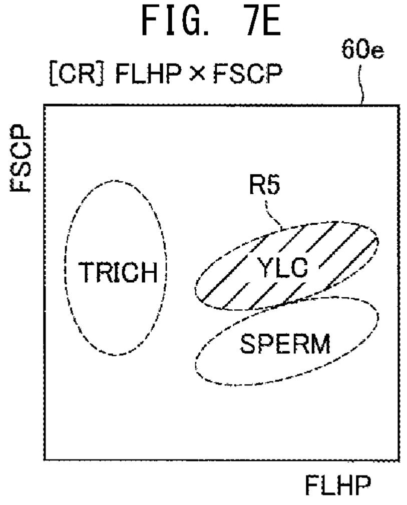
FIG. 7E illustrates distribution data representing a distribution region of yeast-like fungi.

Yeast-like fungi (YLC) are urine particles appearing in a region R5 in distribution data 60*e* of the peak intensity (FLHP) of the side fluorescence signal at the normal sensitivity and the high amplification factor, and the peak intensity (FSCP) of the forward scattered light signal, in the detection data (CR) of the second measurement sample, as shown in FIG. 7E. Particles plotted in the region R5 are counted as yeast-like fungi.

<*Trichomonas vaginalis* (Trich)>

In the first embodiment, for *Trichomonas vaginalis* (Trich), count information 70 about the number of *Trichomonas vaginalis* cells is obtained according to each of the detection data (SF) of the first measurement sample and the detection data (CR) of the second measurement sample.

(a) Detection Data (SF) of First Measurement Sample

Figure 8A:
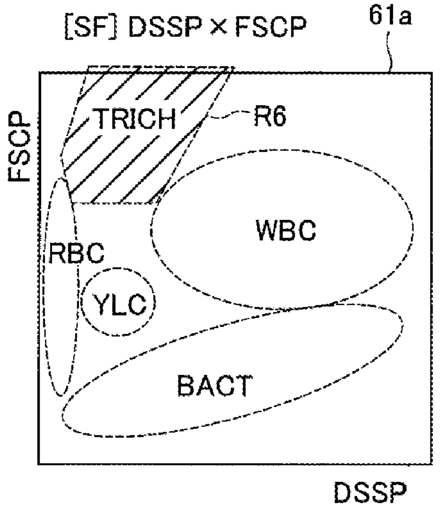
FIG. 8A illustrates distribution data for detecting *Trichomonas vaginalis;*
Figure 8B:
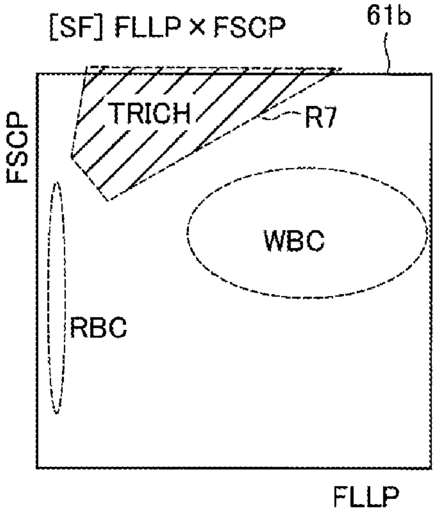
FIG. 8B illustrates distribution data for detecting *Trichomonas vaginalis;*
Figure 8C:
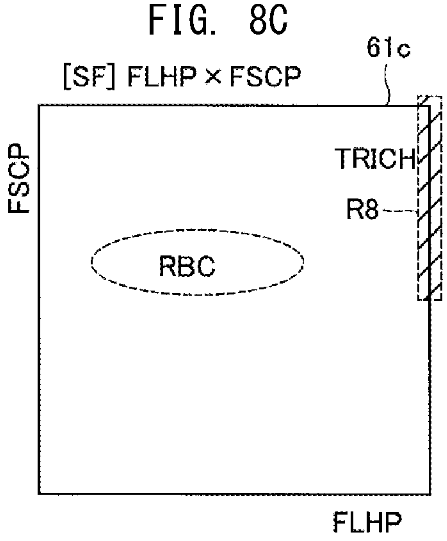
FIG. 8C illustrates distribution data for detecting *Trichomonas vaginalis;*

*Trichomonas vaginalis* (Trich) is distinguished from the other urine particles by a combination of a plurality of kinds of distribution data (61*a*, 61*b*, 61*c*) in the detection data (SF) of the first measurement sample, as shown in FIGS. 8A to 8C.

The distribution data 61*a* shown in FIG. 8A is SF_DSSP×FSCP data. That is, a region R6 in the distribution data 61*a* of the peak intensity (DSSP) of the depolarization side scattered light signal, and the peak intensity (FSCP) of the forward scattered light signal, in the detection data (SF) of the first measurement sample, is set as a first detection region of *Trichomonas vaginalis* (Trich).

The distribution data 61*b* shown in FIG. 8B is SF_FLLP×FSCP data. That is, a region R7 in the distribution data 61*b* of the peak intensity (FLLP) of the side fluorescence signal at the normal sensitivity and the low amplification factor, and the peak intensity (FSCP) of the forward scattered light signal, in the detection data (SF) of the first measurement sample, is set as a second detection region of *Trichomonas vaginalis* (Trich).

The distribution data 61*c* shown in FIG. 8C is SF_FLHP×FSCP data. That is, a region R8 in the distribution data 61*c* of the peak intensity (FLHP) of the side fluorescence signal at the normal sensitivity and the high amplification factor, and the peak intensity (FSCP) of the forward scattered light signal, in the detection data (SF) of the first measurement sample, is set as a third detection region of *Trichomonas vaginalis* (Trich). In the distribution data 61*a* shown in FIG. 8A, the region R6 is close to a distribution region of red blood cells (RBC). In the distribution data 61*c* shown in FIG. 8C, a distribution region of the red blood cells (RBC) is clearly separated from the region R8. *Trichomonas vagi-*

*nalis* and a red blood cell can be clearly distinguished from each other, by taking the distribution data 61*c* into consideration.

In the first embodiment, particles plotted in common in the region R6 in the distribution data 61*a*, the region R7 in the distribution data 61*b*, and the region R8 in the distribution data 61*c* in the detection data (SF) of the first measurement sample, are counted as *Trichomonas vaginalis* detected from the first measurement sample. The obtained count value is set as first count information 70*a* (see FIG. 13).

(b) Detection Data of Second Measurement Sample: CR_FSCW×FLHP

Figure 8D:
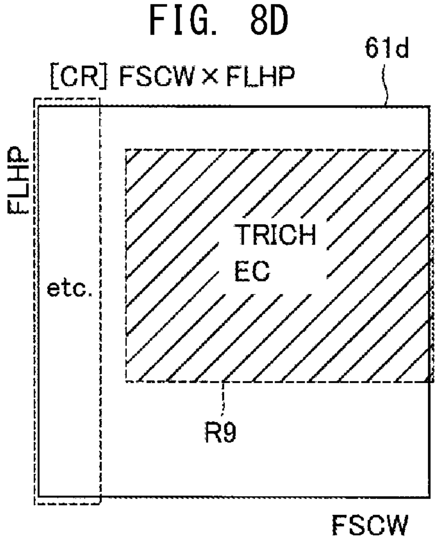
FIG. 8D illustrates distribution data for detecting *Trichomonas vaginalis;*

Distribution data 61*d* shown in FIG. 8D is CR_FSCW×FLHP data. That is, particles plotted in a region R9 in the distribution data 60*d* of the pulse width (FSCW) of the forward scattered light signal and the peak intensity (FLHP) of the side fluorescence signal at the normal sensitivity and the high amplification factor, in the detection data (CR) of the second measurement sample, are counted as *Trichomonas vaginalis* detected from the second measurement sample. The obtained count value is set as second count information 70*b*. Not only *Trichomonas vaginalis* but also epithelial cells (EC) may be included in the region R9.

In the above-described configuration, the analysis unit 20 obtains the count information for each kind of urine particle in the urine specimen 5 based on the detection data obtained from the measurement unit 10.

(Scattergram Obtained by Measuring Actual Specimen)

Figure 9A:
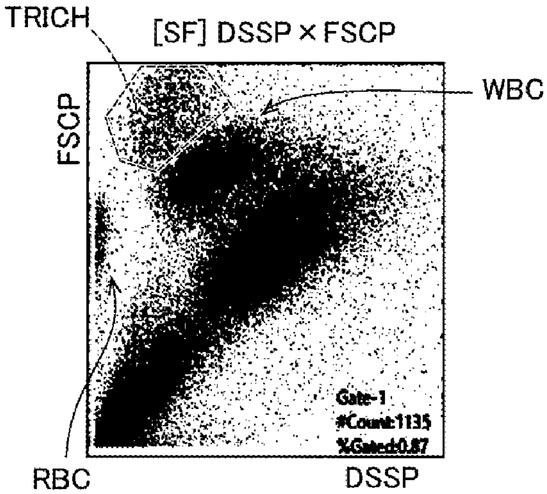
FIG. 9A illustrates distribution data which corresponds to FIG. 8A and is obtained by measuring a *Trichomonas*-positive specimen.
Figure 9B:
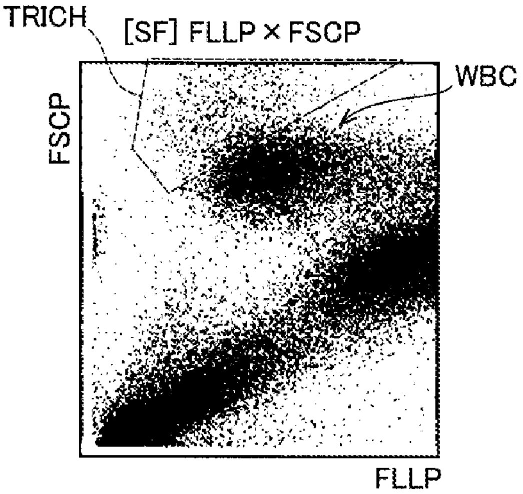
FIG. 9B illustrates distribution data which corresponds to FIG. 8B and is obtained by measuring a *Trichomonas*-positive specimen.

FIG. 9A shows a scattergram of SF_DSSP×FSCP which corresponds to FIG. 8A and is obtained by measuring a *Trichomonas*-positive specimen. FIG. 9B shows a scattergram of SF_FLLP×FSCP which corresponds to FIG. 8B and is obtained by measuring a *Trichomonas*-positive specimen. As shown in FIG. 9A and FIG. 9B, a cluster (TRICH) of *Trichomonas vaginalis* and a cluster (WBC) of white blood cells appear so as to be close to each other. This is because *Trichomonas vaginalis* and a white blood cell are similar in form. In the scattergram shown in FIG. 9A, *Trichomonas vaginalis* and red blood cells (RBC) are plotted so as to be separate from each other. However, in a case where the number of red blood cells is increased, the cluster of *Trichomonas vaginalis* and the cluster of red blood cells become close to each other.

Figure 10:
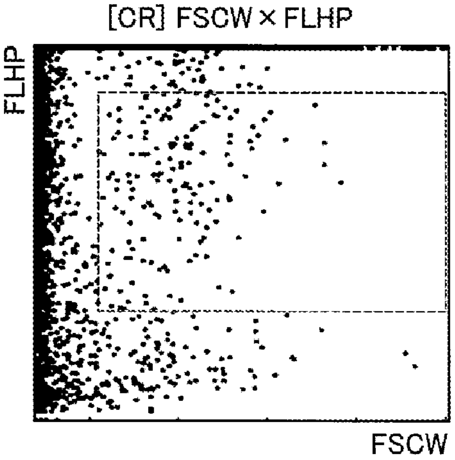
FIG. 10 illustrates distribution data which corresponds to FIG. 8D and is obtained by measuring a *Trichomonas*-positive specimen.

FIG. 10 shows a scattergram of CR_FSCW×FLHP which corresponds to FIG. 8D and is obtained by measuring a *Trichomonas*-positive specimen. As described for FIG. 8D, in the scattergram, *Trichomonas vaginalis* appears in a region indicated by a rectangle (see the dotted-line portion), and epithelial cells also appear in the same region.

Thus, it is difficult to distinguish *Trichomonas vaginalis* from other urine particles and detect *Trichomonas vaginalis*. Therefore, other urine particles as well as *Trichomonas vaginalis* are likely to appear in the regions R6 to R9 shown in FIGS. 8A to 8D. Accordingly, if determination as to suspicion of *Trichomonas* infection is performed based on the plots included in the regions R6 to R9, so-called false-positive determination in which particles different from *Trichomonas vaginalis* in practice are detected as *Trichomonas vaginalis*, may occur.

Figure 11A:
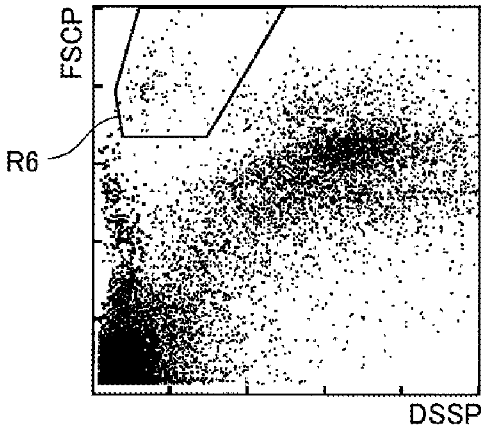
FIG. 11A illustrates a scattergram of a specimen that is confirmed to be *Trichomonas*-positive.
Figure 11B:
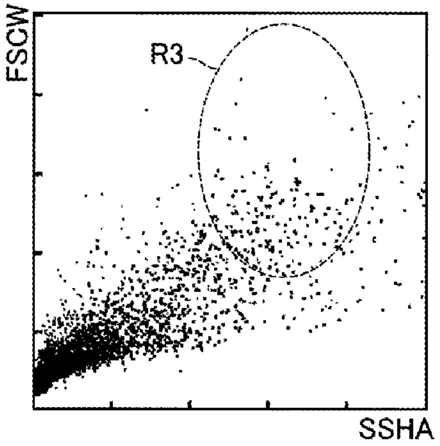
FIG. 11B illustrates a scattergram of a specimen that is confirmed to be *Trichomonas*-positive.
Figure 12A:
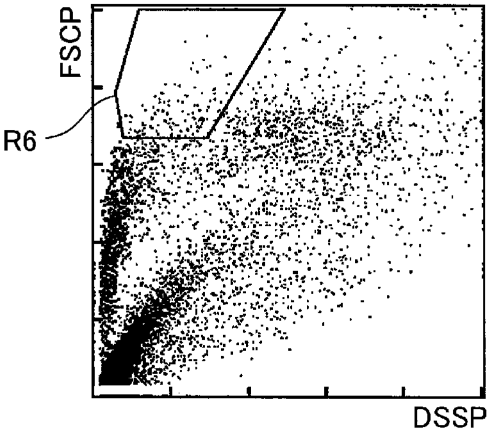
FIG. 12A illustrates a scattergram of a specimen that is not *Trichomonas*-positive.
Figure 12B:
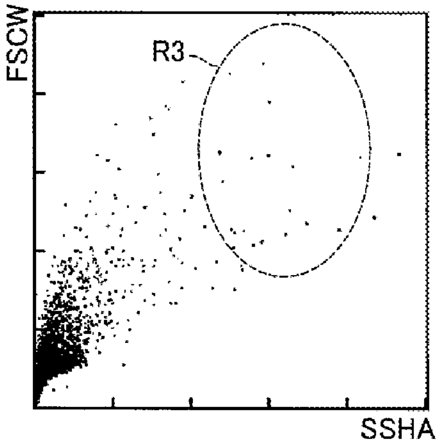
FIG. 12B illustrates a scattergram of a specimen that is not *Trichomonas*-positive.

FIG. 11A and FIG. 11B each show a scattergram of a specimen that is confirmed to be *Trichomonas*-positive. FIG. 12A and FIG. 12B each show a scattergram of a specimen that is not *Trichomonas*-positive. FIG. 11A and FIG. 12A each show a scattergram of SF_DSSP×FSCP which corresponds to FIG. 8A. FIG. 11B and FIG. 12B each show a scattergram of CR_SSHA×FSCW which corresponds to FIG. 7C.

In each of FIG. 11A and FIG. 12A, a significant number of plotted points appear in the region R6 in which *Trichomonas* appears. In these two specimens, plotted points similarly appear in each of the regions R6 to R9. Therefore, if only the number of plotted points included in the regions R6 to R9 is used, the specimen as shown in FIG. 12A may also be determined as being *Trichomonas*-positive.

The inventors have found, as a result of examination, that the number of squamous epithelium cells in urine is significantly increased in a truly positive specimen that is infected with *Trichomonas vaginalis*, whereas the number of squamous epithelium cells is not necessarily increased in a *Trichomonas*-negative specimen. For example, with reference to FIG. 11B, squamous epithelium cells are plotted in a wide range in the *Trichomonas*-positive specimen. Meanwhile, in FIG. 12B, the plotted squamous epithelium cells are very few. Therefore, in the first embodiment, the count information about the number of *Trichomonas vaginalis* cells obtained in the regions R6 to R9 is combined with first information about the number of squamous epithelium cells to enhance accuracy of determination of *Trichomonas* infection.

(Determination Method for Suspicion of *Trichomonas* Infection)

Figure 13:
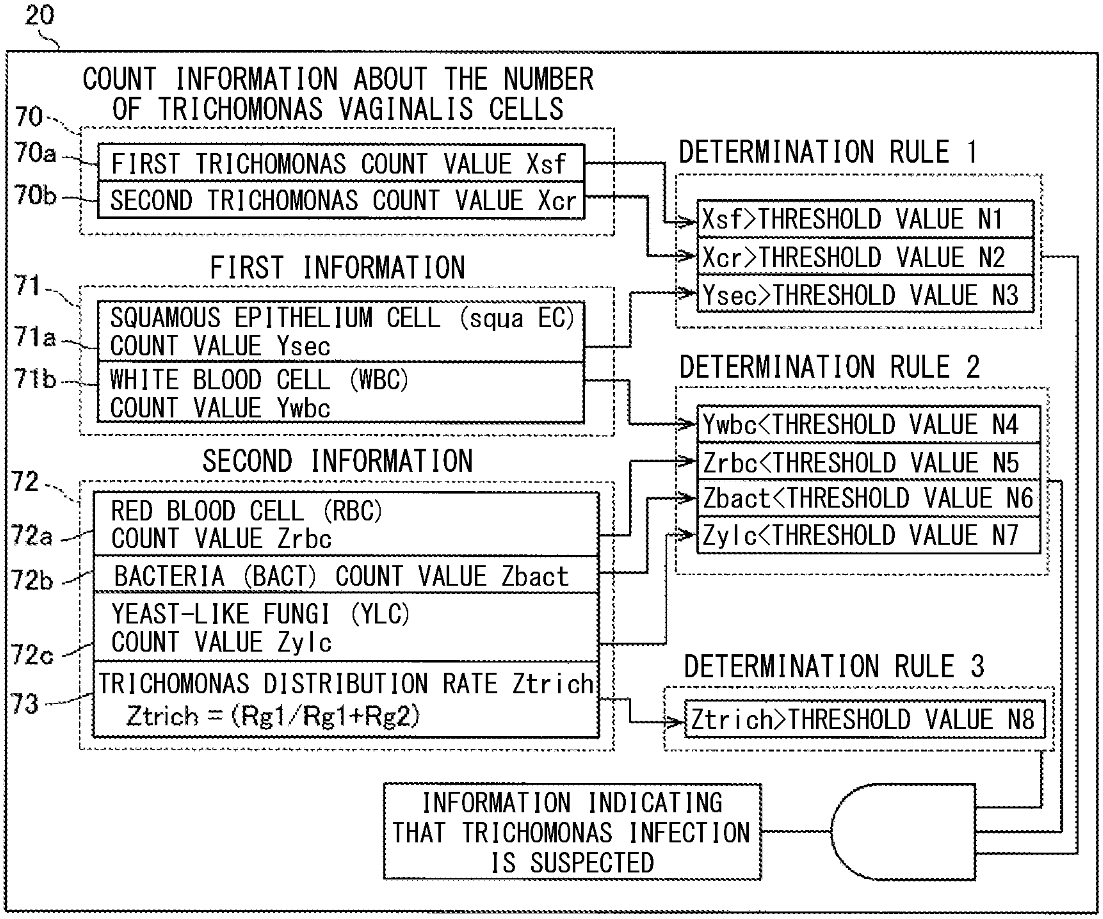
FIG. 13 is a schematic diagram illustrating an outline of determination performed by the analysis unit for suspicion of *Trichomonas* infection.

Next, a determination method for suspicion of *Trichomonas* infection will be described with reference to FIG. 13 and FIG. 14. The analysis unit 20 obtains the count information 70 about the number of *Trichomonas vaginalis* cells, and first information 71 including count information about at least one of the number of squamous epithelium cells and the number of white blood cells, as count information for determination as to suspicion of *Trichomonas* infection, as shown in FIG. 13. In the first embodiment, the analysis unit 20 further obtains second information 72 different from the first information 71.

<Count Information about the Number of *Trichomonas vaginalis* Cells>

In the first embodiment, the count information 70 about the number of *Trichomonas vaginalis* cells includes the first count information 70*a* about the number of *Trichomonas vaginalis* cells that are detected from the urine specimen 5 (that is, detection data (SF) of the first measurement sample) treated with the first reagent 42, and the second count information 70*b* about the number of *Trichomonas vaginalis* cells that are detected from the urine specimen 5 (that is, detection data (CR) of the second measurement sample) treated with the second reagent 43. Hereinafter, the count value of the first count information 70*a* is represented as Xsf, and the count value of the second count information 70*b* is represented as Xcr.

Thus, the count information 70 (the first count information 70*a*, the second count information 70*b*) about the number of *Trichomonas vaginalis* cells is obtained from samples treated with different reagents for the same urine specimen 5, whereby accuracy for distinguishing *Trichomonas vaginalis* from other urine particles in the urine specimen 5 can be enhanced. As a result, reliability of the count information 70 about the number of *Trichomonas vaginalis* cells can be effectively enhanced.

As described above, a part or the entirety of particles counted as the first count information 70*a* and the second count information 70*b* may be other urine particles different from *Trichomonas vaginalis*. In this specification, the "count information about the number of *Trichomonas vaginalis* cells" represents the number of particles having a specific feature parameter set for allowing the urine specimen analyzer to identify *Trichomonas vaginalis*, that is, represents the number of particles appearing in the regions R6 to R9 set for counting *Trichomonas vaginalis* cells, in the first embodiment. The "count information about the number of *Trichomonas vaginalis* cells" does not necessarily represent the number of particles identified as *Trichomonas vaginalis.*

<First Information>

In the first embodiment, the first information 71 includes count information 71*a* about the number of squamous epithelium cells. As described above, in a *Trichomonas*-positive specimen, the number of squamous epithelium cells as well as the number of *Trichomonas vaginalis* cells is significantly increased. In the first embodiment, whether or not the count information 70 about the number of *Trichomonas vaginalis* cells indicates a value greater than a threshold value is determined and whether or not the first information 71 about the number of squamous epithelium cells indicates a value greater than a threshold value is also determined according to a determination rule 1 described below, thereby enhancing accuracy of determination of *Trichomonas* infection. In the first embodiment, count information 71*b* about the number of white blood cells is further used as the first information 71. However, the count information 71*b* about the number of white blood cells is used for determining whether or not white blood cells excessively appear in urine to hinder determination of *Trichomonas* infection, according to a determination rule 2 described below. In this point, the count information 71*b* is different in property from the count information 71*a*. Thus, the number of kinds of the first information 71 serving as an index of reliability of the count information 70 about the number of *Trichomonas vaginalis* cells can be increased. Hereinafter, the count value of the count information 71*a* of squamous epithelium cells is represented as Ysec, and the count value of the count information 71*b* of white blood cells is represented as Ywbc.

<Second Information>

The second information 72 includes information for inhibiting false-positive determination as to suspicion of *Trichomonas* infection. Thus, false-positive determination as to suspicion of *Trichomonas* infection can be reduced by taking the second information 72 into consideration.

Specifically, the second information 72 includes count information about the number of other urine particles different from *Trichomonas vaginalis*, squamous epithelium cells, and white blood cells. Thus, reliability of the count information 70 about the number of *Trichomonas vaginalis* cells can be evaluated based on the number of interfering substances that cause false-positive determination, by taking into consideration the count information about the number of other urine particles as the second information 72.

The information for inhibiting false-positive determination as to suspicion of *Trichomonas* infection includes the count information about the number of at least one of other urine particles that interfere with detection of *Trichomonas vaginalis*. The other urine particles coexist with a target particle (in this case, *Trichomonas vaginalis*) in the urine specimen 5, and become interfering substances that are likely to change the count value of the target particles. Therefore, in a case where the interfering substance can be determined to affect detection of *Trichomonas vaginalis*, influence of the interfering substance is taken into consideration and information 80 about suspicion of *Trichomonas* infection can be outputted.

The at least one of the other urine particles that interfere with detection of *Trichomonas vaginalis* includes at least one of red blood cells, bacteria, and yeast-like fungi. In the first embodiment, a plurality of kinds of urine particles among these other urine particles are set in the second information 72. Specifically, the second information 72 includes count information 72*a* of red blood cells, count information 72*b* of bacteria, and count information 72*c* of yeast-like fungi. Thus, reliability of the information 80 about suspicion of *Trichomonas* infection can be inhibited from being degraded due to existence of the interfering substances. Hereinafter, the count value of the count information 72*a* of red blood cells is represented as Zrbc, the count value of the count information 72*b* of bacteria is represented as Zbact, and the count value of the count information 72*c* of yeast-like fungi is represented as Zylc.

The second information 72 includes information about a distributed state of *Trichomonas vaginalis*, in the distribution data 60 representing the distribution of urine particles in the urine specimen 5. Thus, reliability of the count information 70 about the number of *Trichomonas vaginalis* cells can be determined based on the distribution of *Trichomonas vaginalis* in the distribution data 60. Therefore, accurate determination as to suspicion of *Trichomonas* infection can be performed by also taking into consideration information about the distributed state of *Trichomonas vaginalis.*

The information about the distributed state of *Trichomonas vaginalis* is specifically information 73 indicating distribution deviation of *Trichomonas vaginalis* to a side close to the distribution region of other urine particles, in the distribution region R6 of *Trichomonas vaginalis.*

Figure 14:
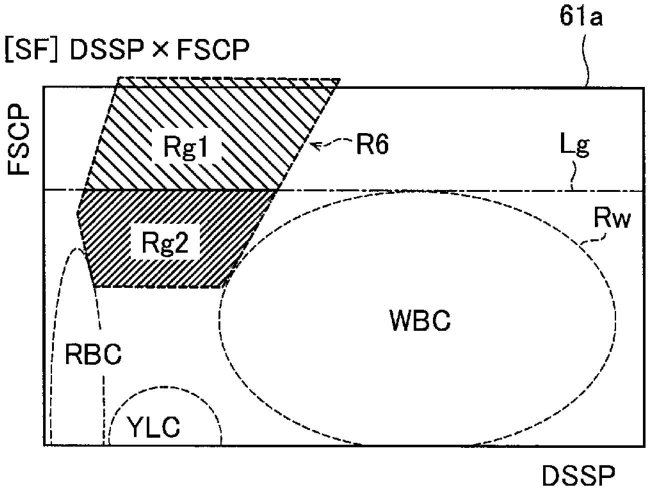
FIG. 14 illustrates distribution data for explaining a method for obtaining information indicating distribution deviation of *Trichomonas vaginalis;*

FIG. 14 illustrates, in an enlarged manner, the periphery of the distribution region (regions R6) of *Trichomonas vaginalis* in the distribution data 61*a* for obtaining the first count information 70*a* of *Trichomonas vaginalis* as shown in FIG. 8A. The region R6 is positioned so as to be close to a distribution region Rw of white blood cells (WBC) on the lower right side (low value side of FSCP and high value side of DSSP) of the distribution data 61*a*. Therefore, urine particles that are actually white blood cells may be plotted so as to be mixed in the region R6 in the distribution data 61*a*. Accordingly, in the first embodiment, the distribution region of other urine particles include the distribution region Rw of white blood cells in the distribution data 61*a.*

An imaginary line Lg indicating an upper limit position, in FSCP, of the distribution region Rw of white blood cells (WBC) in the distribution data 61*a* is assumed in order to evaluate possibility that white blood cells are mixed in the region R6. The imaginary line Lg indicates that, in the distribution data 61*a*, in a case where white blood cells are plotted, the white blood cells are plotted below the imaginary line Lg. Therefore, a partial region Rg1 and a partial region Rg2 into which the region R6 is divided by the imaginary line Lg are set. The partial region Rg1 is a portion of the region R6 which is farther from the distribution region Rw of white blood cells, and the partial region Rg2 is a portion of the region R6 which is closer to the distribution region Rw of white blood cells. In a case where white blood cells are mixed in the region R6, although the white blood cells may be plotted in the partial region Rg2 below the imaginary line Lg, the white blood cells are hardy plotted in the partial region Rg1 above the imaginary line Lg.

Thus, in a case where the plotted points belonging to the region R6 appear unevenly in the partial region Rg2, white blood cells are likely to be mixed in the region R6. Therefore, reliability of the first count information 70*a* representing counted *Trichomonas vaginalis* cells can be evaluated as being low. Meanwhile, in a case where the plotted points belonging to the region R6 appear unevenly in the partial region Rg1, white blood cells are unlikely to be mixed in the region R6. Therefore, reliability of the first count information 70*a* can be evaluated as being high.

The analysis unit 20 obtains a distribution rate Ztrich of the plotted points belonging to the partial region Rg1 from the distribution region Rw of white blood cells, in plotted points belonging to the region R6, as the information 73 indicating distribution deviation of *Trichomonas vaginalis* to a side close to the distribution region Rw of other urine particles in the distribution region R6 of *Trichomonas vaginalis*.

The distribution rate Ztrich is represented as {the number of plotted points belonging to the partial region Rg1/(the number of plotted points belonging to the partial region Rg2)+(the number of plotted points belonging to the partial region Rg1)}.

{(The number of plotted points belonging to the partial region Rg2)+(the number of plotted points belonging to the partial region Rg1)} means the entirety of the plotted points belonging to the region R6. The lower the value of the distribution rate Ztrich is, the greater the deviation of the plotted points belonging to the region R6 to the partial region Rg2 side is, and possibility of mixing white blood cells is evaluated as being high. The higher the value of the distribution rate Ztrich is, the less the deviation of the plotted points belonging to the region R6 to the partial region Rg2 side is, and possibility of mixing white blood cells is evaluated as being low.

(Determination Rule)

In the first embodiment, as shown in FIG. 13, the determination rule for suspicion of *Trichomonas* infection is set by combining the above-described information. The determination rule represents a rule for determining that the urine specimen 5 is suspected of *Trichomonas* infection (positive), based on the obtained detection data.

In the first embodiment, the analysis unit 20 obtains the count information 70 about the number of *Trichomonas vaginalis* cells, and the first information 71 including the count information about at least one of the number of squamous epithelium cells and the number of white blood cells, based on the detection data of urine particles in the urine specimen 5, and outputs the information 80 about suspicion of *Trichomonas* infection, based on at least the count information 70 about the number of *Trichomonas vaginalis* cells and the first information 71.

In addition to the number of *Trichomonas vaginalis* cells, the number of each of squamous epithelium cells and white blood cells appearing in the urine specimen 5 of a patient who suffers from *Trichomonas* infection is significantly increased. Therefore, in a case where the value of the count information obtained as the first information 71 is high, reliability of the count information 70 about the number of *Trichomonas vaginalis* cells can be determined to be high. Meanwhile, in a case where the value of the count information obtained as the first information 71 is low, reliability of the count information 70 about the number of *Trichomonas vaginalis* cells can be determined to be low. Reliability of the count information 70 about the number of *Trichomonas vaginalis* cells can be enhanced based on the first information 71 serving as an index of reliability of the count information 70 about the number of *Trichomonas vaginalis* cells.

In the first embodiment, three determination rules are set for determination as to suspicion of *Trichomonas* infection. The determination rule 1 is a determination rule for performing determination as to suspicion of *Trichomonas* infection, based on the count information 70 about the number of *Trichomonas vaginalis* cells and the first information 71. Specifically, according to the determination rule 1, in a case where the count information 70 about the number of *Trichomonas vaginalis* cells satisfies a condition and the count information belonging to the first information 71 satisfies a condition, determination that *Trichomonas* infection is suspected is made as the information 80 about suspicion of *Trichomonas* infection. In a case where the first information 71 serving as an index of reliability of the count information 70 about the number of *Trichomonas vaginalis* cells satisfies a condition in addition to the count information 70 about the number of *Trichomonas vaginalis* cells satisfying a condition, information indicating that *Trichomonas* infection is suspected is outputted, whereby reliability of the information indicating that *Trichomonas* infection is suspected can be enhanced.

A determination rule 2 and a determination rule 3 are each a determination rule including the second information 72. Thus, in the first embodiment, the information 80 about suspicion of *Trichomonas* infection is outputted based on the second information 72 in addition to the count information 70 about the number of *Trichomonas vaginalis* cells and the first information 71. Thus, reliability of the information 80 about suspicion of *Trichomonas* infection can be determined by further taking into consideration the other second information 72 in addition to the first information 71 serving as an index of reliability of the count information 70 about the number of *Trichomonas vaginalis* cells.

The determination rule 2 and the determination rule 3 are each a determination rule for reducing, based on at least the second information 72, possibility of false-positive determination in the determination results based on the determination rule 1. Therefore, the determination rule 2 and the determination rule 3 are each a determination rule for prohibiting output of information indicating that *Trichomonas* infection is suspected in a case where a condition in each of the determination rule 2 and the determination rule 3 is satisfied. That is, even in a case where *Trichomonas* infection is determined to be suspected according to the determination rule 1, when a condition in either the determination rule 2 or the determination rule 3 is satisfied, non-positive (negative or non-determinable) determination is made due to possibility of false-positive determination. However, for easy understanding, a condition for outputting determination that *Trichomonas* infection "is suspected" will be described below also for the determination rule 2 and the determination rule 3.

<Determination Rule 1>

In the determination rule 1 in an example shown in FIG. 13, the first count information 70*a*, the second count information 70*b*, and the count information of squamous epithelium cells as the first information 71 are compared with corresponding threshold values, respectively.

That is, the determination rule 1 includes the following criteria (1) to (3).

(1) the count value Xsf of the first count information 70*a* is greater than a threshold value N1 (Xsf>N1), (2) the count value Xcr of the second count information 70*b* is greater than a threshold value N2 (Xcr>N2), and (3) the count value Ysec of the count information of squamous epithelium cells is greater than a threshold value N3 (Ysec>N3).

In a case where all of the criteria (1) to (3) in the determination rule 1 are satisfied, *Trichomonas* infection is "determined to be suspected" according to the determination rule 1. In a case where one or more of the three criteria in the determination rule 1 is not satisfied, it is determined that "*Trichomonas* infection is not suspected or determination is impossible" according to the determination rule 1.

The threshold values N1 to N3 applied to the determination rule 1 will be described below. The threshold value N3 of the count value Ysec of the first information 71 is basically at least greater than the threshold value N1 of the count value Xsf of the first count information 70*a* in a non-hemolyzed condition. This principle applies to a first mode and a third mode described below.

That is, the determination rule 1 includes comparison between the count value X (Xsf) of the count information (the first count information 70*a*) about the number of *Trichomonas vaginalis* cells in a non-hemolyzed condition (the first measurement sample) and the first threshold value N1, and comparison between the count value Y (Ysec) of the first information 71 and the second threshold value N3 greater than the first threshold value N1. In a case where criteria of the count value X (Xsf)> the threshold value N1 and the count value Y (Ysec)> the threshold value N3 are satisfied, *Trichomonas* infection is determined to be suspected.

That is, since the number of *Trichomonas vaginalis* cells appearing in urine is small, a threshold value (low threshold value) is preferably set so as to allow *Trichomonas vaginalis* to be detected even in a case where the number of *Trichomonas vaginalis* cells appearing in urine is very small. Meanwhile, since *Trichomonas vaginalis* is similar in form to a white blood cell and a red blood cell, the number of the urine specimens 5 falsely determined to be positive may be increased when the threshold value is set to be low. Accordingly, determination accuracy can be enhanced by adding the first information 71 (whether or not squamous epithelium cells or white blood cells appear in urine) to determination criteria for suspicion of *Trichomonas* infection. Meanwhile, since squamous epithelium cells or white blood cells are likely to be included in urine even when a urinary system is not abnormal, the second threshold value (N3) of the count value of the first information 71 is made greater than the first threshold value (N1) of the count value of *Trichomonas vaginalis* cells, whereby the false positive determination can be reduced in a case where the count value of the first information 71 is increased due to a cause different from *Trichomonas* infection.

<Determination Rule 2>

In the determination rule 2 in the example shown in FIG. 13, the count information 72*a* of red blood cells (RBC), the count information 72*b* of bacteria (BACT), and the count information 72*c* of yeast-like fungi (YLC) as the second information 72 are compared with corresponding threshold values, respectively. Furthermore, according to the determination rule 2, the count information 71*b* of white blood cells (WBC) as the first information 71 is compared with a threshold value. This comparison of the first information 71 with the threshold value may be included in the above-described determination rule 1. A criterion for outputting determination that *Trichomonas* infection "is suspected" according to the determination rule 2 will be firstly described.

That is, the determination rule 2 includes the following criteria (4) to (7).

(4) the count value Ywbc of white blood cells is less than a threshold value N4 (Ywbc<N4), (5) the count value Zrbc of red blood cells is less than a threshold value N5 (Zrbc<N5), (6) the count value Zbact of bacteria is less than a threshold value N6 (Zbact<N6), and (7) the count value Zylc of yeast-like fungi is less than a threshold value N7 (Zylc<N7).

In a case where all of the criteria (4) to (7) in the determination rule 2 are satisfied, *Trichomonas* infection is "determined to be suspected" according to the determination rule 2. In a case where one or more of the four criteria (4) to (7) in the determination rule 2 is not satisfied, it is determined that *Trichomonas* infection "is not suspected or determination is impossible".

In the first embodiment, specific examples of the threshold values are N4=10000/μL, N5=1000/μL, N6=100000/μL, and N7=300/μL.

Therefore, according to the determination rule 2, "the condition for prohibiting output of determination that *Trichomonas* infection "is suspected" is that one or more of the criteria (4) to (7) that the number of urine particles is small is not satisfied. In a situation in which a large number of urine particles that hinder identification of *Trichomonas vaginalis* are present, identification of *Trichomonas vaginalis* is difficult, so that the determination result becomes uncertain if determination of *Trichomonas* infection is performed based on the count information 70 about the number of *Trichomonas vaginalis* cells. Therefore, in a case where whether or not the count information of each of a plurality of kinds of interfering substances that cause false-positive determination satisfies a condition is determined, and one or more of the conditions is satisfied, output of determination that *Trichomonas* infection "is suspected" is prohibited, whereby reliability of the information 80 about suspicion of *Trichomonas* infection can be inhibited from being degraded. Thus, in the first embodiment, in a case where the count information of one or more kinds of a plurality of kinds of urine particles satisfies a condition, information indicating that *Trichomonas* infection is suspected is prohibited from being outputted as the information 80 about suspicion of *Trichomonas* infection.

<Determination Rule 3>

In the determination rule 3 in the example shown in FIG. 13, as the second information 72, the information 73 indicating distribution deviation of *Trichomonas vaginalis* to a side close to the distribution region of the other urine particles is compared with a threshold value. A criterion for outputting determination that *Trichomonas* infection "is suspected" according to the determination rule 3 will be firstly described.

That is, the determination rule 3 includes the following criterion (8).

(8) the distribution rate Ztrich of *Trichomonas vaginalis* belonging to the partial region Rg1 is greater than a threshold value N8 (Ztrich>N8).

(in which Ztrich={the number of plotted points belonging to the partial region Rg1/(the number of plotted points belonging to the partial region Rg2)+(the number of plotted points belonging to the partial region Rg1)} is satisfied).

In a case where the criterion (8) is satisfied, *Trichomonas* infection is "determined to be suspected" according to the determination rule 3. In a case where the criterion (8) in the determination rule 3 is not satisfied, it is determined that *Trichomonas* infection "is not suspected or determination is impossible". In the first embodiment, a specific example of the threshold value is N8=0.1.

Therefore, the "condition for prohibiting output of determination that *Trichomonas* infection "is suspected"" according to the determination rule 3 is that the criterion (8) is not satisfied. Thus, in the first embodiment, in a case where the distribution data 61*a* indicates distribution deviation of *Trichomonas vaginalis* to a side close to the distribution region Rw of other urine particles (white blood cells) in the distribution region R6 (see FIG. 14) of *Trichomonas vaginalis*, information indicating that *Trichomonas* infection is suspected is prohibited from being outputted as the information 80 about suspicion of *Trichomonas* infection. Thus, in a case where other urine particles having features, such as a size and a form, similar to those of *Trichomonas vaginalis* are likely to be mixed in the distribution region (the region R6) of *Trichomonas vaginalis* in the obtained distribution data 61*a*, information having low reliability can be inhibited from being outputted.

As described above, the distribution region of other urine particles includes the distribution region Rw of white blood cells in the distribution data 60. Thus, in a case where white blood cells having features, such as a size and a form, similar to those of *Trichomonas vaginalis* are mixed in the distribution region of *Trichomonas vaginalis*, information having low reliability can be inhibited from being outputted, by taking into consideration possibility of mixing white blood cells.

<Specific Examples of the Threshold Values N1 to N3 in the Determination Rule 1>

In the first embodiment, for the threshold values N1 to N3 (see FIG. 13) used for the determination rule 1, selection of a mode from among a plurality of modes having different set values as the threshold values can be received. The analysis unit 20 receives selection of the mode through an input operation using the input unit 20*b* (see FIG. 1).

In an example shown in FIG. 15, the plurality of modes include a first mode, a second mode, and a third mode. Each of the plurality of modes has a threshold value set in which the threshold values N1, N2, N3 are defined. The threshold value set in each of the plurality of modes is stored in the storage unit 22 in advance.

The first mode as a standard mode has a first threshold value set 75*a*. In the first threshold value set 75*a*, the threshold value N1=1.0/μL, the threshold value N2=5.0/μL, and the threshold value N3=5.0/μL are set. The analysis unit 20 applies the first threshold value set 75*a* for the threshold values N1 and N2 for the count information 70 about the number of *Trichomonas vaginalis* cells, and the threshold value N3 for the first information 71, according to the first mode being selected.

The second mode as a sensitivity-oriented mode has a second threshold value set 75*b* including threshold values that are set to be lower than the values of the first threshold value set 75*a*. In the second threshold value set 75*b*, the threshold value N1=1.0/μL, the threshold value N2=1.0/μL, and the threshold value N3=1.0/μL are set. In the second threshold value set 75*b*, the threshold value N2 and threshold value N3 are less than those of the first threshold value set 75*a*. The analysis unit 20 applies the second threshold value set 75*b* for the threshold values N1 and N2 for the count information 70 about the number of *Trichomonas vaginalis* cells and the threshold value N3 for the first information 71 according to the second mode being selected.

The third mode as a specificity-oriented mode has a third threshold value set 75*c* including threshold values that are set to be higher than those of the first threshold value set 75*a*. In the third threshold value set 75*c*, the threshold value N1=10.0/μL, the threshold value N2=20.0/μL, and the threshold value N3=20.0/μL are set. In the third threshold value set 75*c*, the threshold value N1, the threshold value N2, and the threshold value N3 are greater than those of the first threshold value set 75*a*. The analysis unit 20 applies the third threshold value set 75*c* for the threshold values N1 and N2 for the count information 70 about the number of *Trichomonas vaginalis* cells and the threshold value N3 for the first information 71 according to the third mode being selected.

Thus, the second threshold value set 75*b* and the third threshold value set 75*c* are set such that sensitivity and specificity, respectively, about suspicion of *Trichomonas* infection are higher than those of the first threshold value set 75*a*.

As described above, in the determination rule 1, in a case where all of the count values of the count information 70 about the number of *Trichomonas vaginalis* cells and the count value of the first information 71 are greater than or equal to the applied corresponding threshold values N1, N2, N3, *Trichomonas* infection is determined to be suspected. Therefore, by setting a plurality of modes having different threshold value sets, a user is allowed to autonomously select a mode and perform determination as to suspicion of *Trichomonas* infection. Therefore, for example, in a case where the user selects the threshold value set 75*b* for high sensitivity (low threshold value) about suspicion of *Trichomonas* infection, among the first threshold value set 75*a* and the second threshold value set 75*b*, information that can make greater contribution to early detection of *Trichomonas* infection can be provided. For example, in a case where the user selects the threshold value set 75*a* for high specificity (high threshold value) about suspicion of *Trichomonas* infection, among the first threshold value set 75*a* and the second threshold value set 75*b*, information that can further reduce possibility of false-positive determination of *Trichomonas* infection can be provided.

In the configuration in which the first mode (the first threshold value set 75*a*) as the standard mode, the second mode (the second threshold value set 75*b*) as the sensitivity-oriented mode, and the third mode (the third threshold value set 75*c*) as the specificity-oriented mode, are set, the user is allowed to switch between the first mode as the standard mode, the second mode as the sensitivity-oriented mode which is likely to contribute to early detection, and the third mode as the specificity-oriented mode in which certainty of analysis result is preferential, merely by selecting the mode. Therefore, information about suspicion of *Trichomonas* infection can be provided according to the needs of the user.

(Information about Suspicion of *Trichomonas* Infection)

FIG. 16 is a schematic diagram illustrating an example of a screen on the display unit 20*c* for displaying the analysis result of the analysis unit 20. The analysis unit 20 outputs, to the display unit 20*c*, the information 80 about suspicion of *Trichomonas* infection, as shown in FIG. 16. That is, the analysis unit 20 causes the display unit 20*c* to display an analysis result screen 81 including the information 80 about suspicion of *Trichomonas* infection.

The analysis result screen 81 is a screen for displaying a detection result and an analysis result for one urine specimen 5 having been analyzed, and includes a count information display column 82 and an information display column 83. On the count information display column 82, the count information as a detection result of urine particles detected from the urine specimen 5 is individually displayed for each kind of the urine particle. In an example shown in FIG. 16, the count information display column 82 includes an item column 82*a* indicating item names such as red blood cell (RBC), white blood cell (WBC), epithelial cell (EC), squamous epithelium cell (SquaEC), non-squamous epithelium cell (NonSEC), cast (CAST), BACT (bacteria), and yeast-like fungi (YLC), and a result column 82*b* indicating the count values of the urine particles displayed in the item column 82*a*. The column at the right end of the count information display column 82 indicates a unit of the count value. A specific example of a method for counting epithelial cells (EC), non-squamous epithelium cells (NonSEC), and casts (CAST) indicated in the item column 82*a* is not described in this specification. The values in the result column 82*b* are not shown.

In the information display column 83, information about suspicion of each disease or the like that is determined based on the count information of the urine particles which are detected from the urine specimen 5 is displayed. In the first embodiment, the information 80 about suspicion of *Trichomonas* infection is displayed in the information display column 83.

In the first embodiment, the information 80 about suspicion of *Trichomonas* infection includes information indicating that *Trichomonas* infection is suspected. In a case where the detection data of urine particles in the urine specimen 5 satisfies all of the criteria (see FIG. 13) of the determination rule 1 to the determination rule 3 described above, the analysis unit 20 outputs, to the information display column 83, the information indicating that *Trichomonas* infection is suspected.

In this case, in the example shown in FIG. 16, "Trich" representing *Trichomonas* infection as an analysis item, and "*Trichomonas*?" indicating that *Trichomonas* infection is suspected are displayed in the information display column 83. Thus, information indicating that *Trichomonas* infection is suspected is provided to the user for the analysis item of *Trichomonas* infection.

In the first embodiment, in a case where the detection data of urine particles in the urine specimen 5 does not satisfy one or more of the determination rule 1 to the determination rule 3 described above, the analysis unit 20 does not output the information 80 about suspicion of *Trichomonas* infection, to the information display column 83. That is, in this case, each of "Trich" and "*Trichomonas*?" is not displayed in the information display column 83.

In a case where the detection data of the urine particles in the urine specimen 5 does not satisfy one or more of the determination rule 1 to the determination rule 3 described above, the analysis unit 20 may output, to the information display column 83, information indicating that *Trichomonas* infection is not suspected or determination is impossible.

(Operation Performed by Urine Specimen Analyzer)

An operation performed by the urine specimen analyzer 100 of the first embodiment will be described below with reference to FIG. 17 to FIG. 22.

Figure 17:
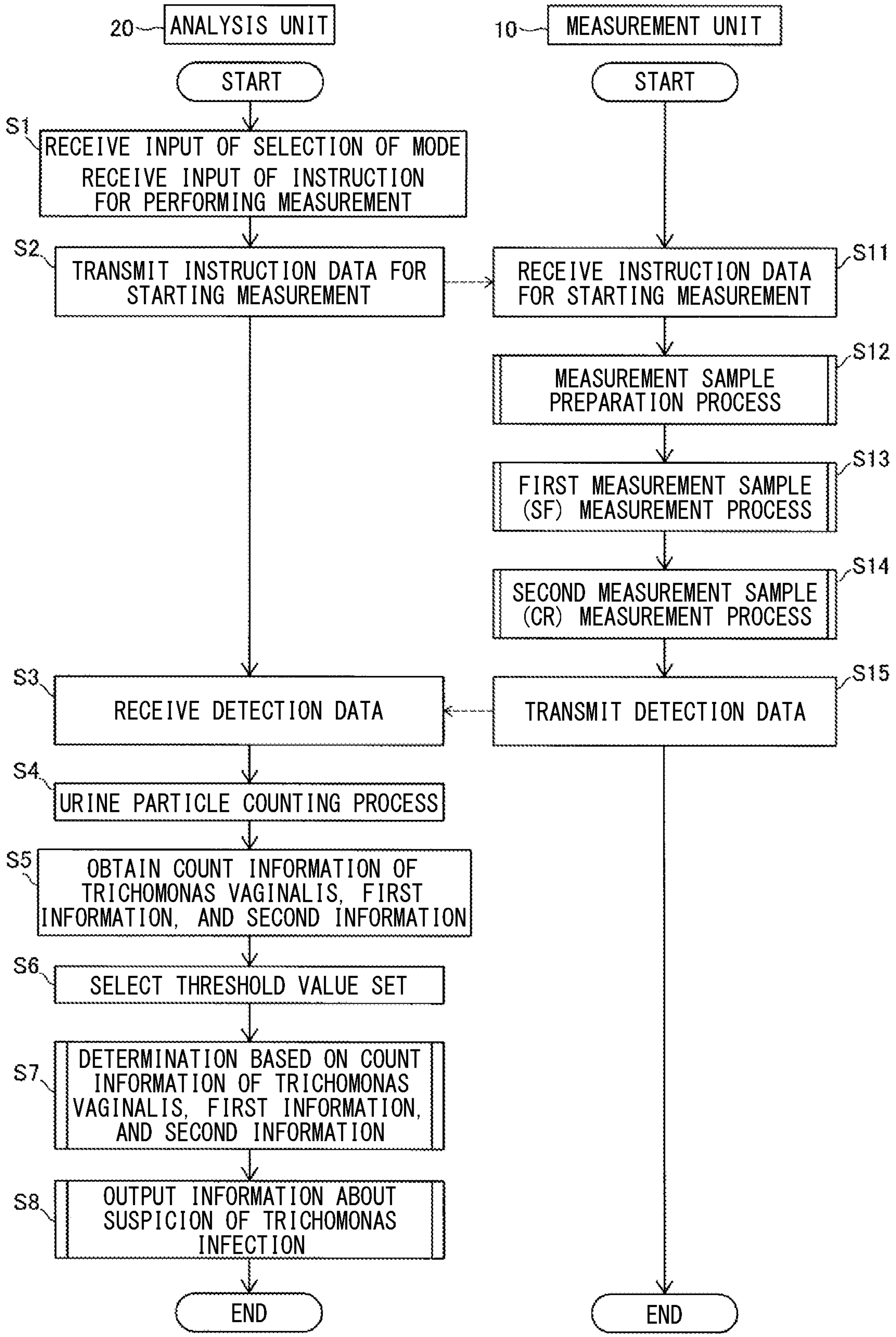
FIG. 17 is a flow chart showing an operation performed by the urine specimen analyzer.

FIG. 17 is a flow chart showing a flow of a specimen measurement process performed by the urine specimen analyzer 100. The process for controlling the analysis unit 20 is performed by the processor 21. The process for controlling the measurement unit 10 is performed by the microcomputer 51. In the following description, each unit of the urine specimen analyzer 100 is shown in FIG. 1 to FIG. 5.

Firstly, in step S1, the processor 21 of the analysis unit 20 receives an instruction from a user for performing measurement, through an input operation using the input unit 20*b*. The processor 21 receives selection of a mode for specifying a threshold value set from among the first mode to the third mode shown in FIG. 15, through an input operation using the input unit 20*b*. The processor 21 causes the storage unit 22 to store information specifying the selected mode. The selection of the mode may be received at any time before the measurement is performed. In step S2, the processor 21 operates to transmit the instruction data for instructing the measurement unit 10 to start the measurement.

In step S11, the microcomputer 51 receives the instruction data for starting the measurement from the analysis unit 20. Upon receiving the instruction data for starting the measurement, the microcomputer 51 operates the measurement unit 10 so as to perform a measurement sample preparation process (step S12), a first measurement sample (SF) measurement process (step S13), and a second measurement sample (CR) measurement process (step S14). Through the first measurement sample (SF) measurement process and the second measurement sample (CR) measurement process, detection data for one urine specimen 5 is generated. The detection data is stored in the memory 50*e*.

In step S15, the microcomputer 51 operates to transmit the detection data (SF) and the detection data (CR) stored in the memory 50*e*, to the analysis unit 20.

In step S3, the processor 21 of the analysis unit 20 receives the detection data transmitted from the measurement unit 10.

In step S4, the processor 21 performs a process of counting urine particles based on the detection data. That is, the processor 21 classifies a signal of each particle for each kind of the urine particle, from the detection data, by using a combination of the feature parameters shown in FIG. 7 and FIG. 8, and generates count information of each kind of the urine particle.

In step S5, the processor 21 obtains each of the count information 70 (the first count information 70*a*, the second count information 70*b*) about *Trichomonas vaginalis*, and information (the first information 71, the second information 72), which are generated in step S4.

In step S6, information about selection of the mode received in step S1 is obtained from the storage unit 22, and the threshold values N1 to N3 defined by the threshold value set corresponding to the selected mode among the threshold value sets 75*a* to 75*c* (see FIG. 15) are set.

In step S7, the processor 21 performs determination as to *Trichomonas* infection based on the obtained count information 70 (the first count information 70*a*, the second count information 70*b*) about *Trichomonas vaginalis*, and the first information 71 and the second information 72 having been obtained. The determination is performed based on the determination rule 1, the determination rule 2, and the determination rule 3 shown in FIG. 13. The processor 21 generates the information 80 about suspicion of *Trichomonas* infection, as a result of the determination.

In step S8, the processor 21 outputs the information 80 about suspicion of *Trichomonas* infection. Thus, the specimen measurement process for one urine specimen 5 is completed.

<Measurement Sample Preparation Process>

The measurement sample preparation process in step S12 shown in FIG. 17 will be described. The measurement sample preparation process is performed by the microcomputer 51 of the measurement unit 10. In the following description, each unit of the urine specimen analyzer 100 is shown in FIG. 1 to FIG. 5.

Figure 18:
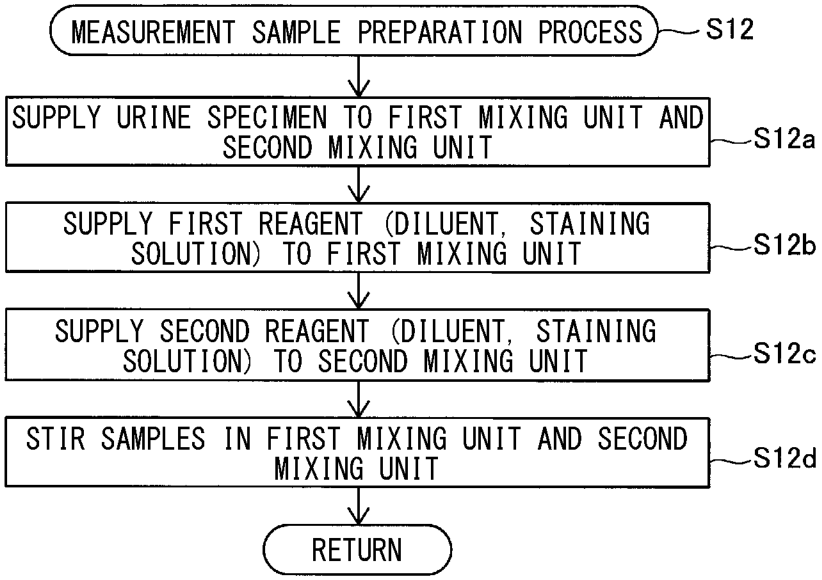
FIG. 18 is a flow chart showing a measurement sample preparation process in FIG. 17.

In step S12*a* in FIG. 18, the microcomputer 51 controls the specimen distributing unit 45 so as to suction a predetermined amount of the urine specimen 5 from the specimen container 14 by using the suction tube 46, and dispenses the predetermined amount of the urine specimen 5 into the first mixing unit 41*a* and the second mixing unit 41*b*.

In step S12*b*, the microcomputer 51 controls the sample preparation unit 40 so as to dispense a predetermined amount of the first reagent 42 (the first staining solution 42*a* and the first diluent 42*b*) into the first mixing unit 41*a*. In step S12*c*, the microcomputer 51 controls the sample preparation unit 40 so as to dispense a predetermined amount of the second reagent 43 (the second staining solution 43*a* and the second diluent 43*b*) into the second mixing unit 41*b*.

Each of the first mixing unit 41*a* and the second mixing unit 41*b* is heated to a predetermined temperature by a not-illustrated heater. In this state, in step S12*d*, the microcomputer 51 controls the sample preparation unit 40 so as to stir a mixture in each mixing unit by using a propeller-shaped stirrer (not shown).

Thus, the first measurement sample for measuring anucleate particles is prepared in the first mixing unit 41*a*, and the second measurement sample for measuring nucleate particles is prepared in the second mixing unit 41*b*. When the process step of step S12*d* ends, the microcomputer 51 returns the process to a main routine in FIG. 17.

<First Measurement Sample (SF) Measurement Process>

The first measurement sample (SF) measurement process in step S13 shown in FIG. 17 will be described. The first measurement sample (SF) measurement process is performed by the microcomputer 51 of the measurement unit 10. In the following description, each unit of the urine specimen analyzer 100 is shown in FIG. 1 to FIG. 5.

Figure 19:
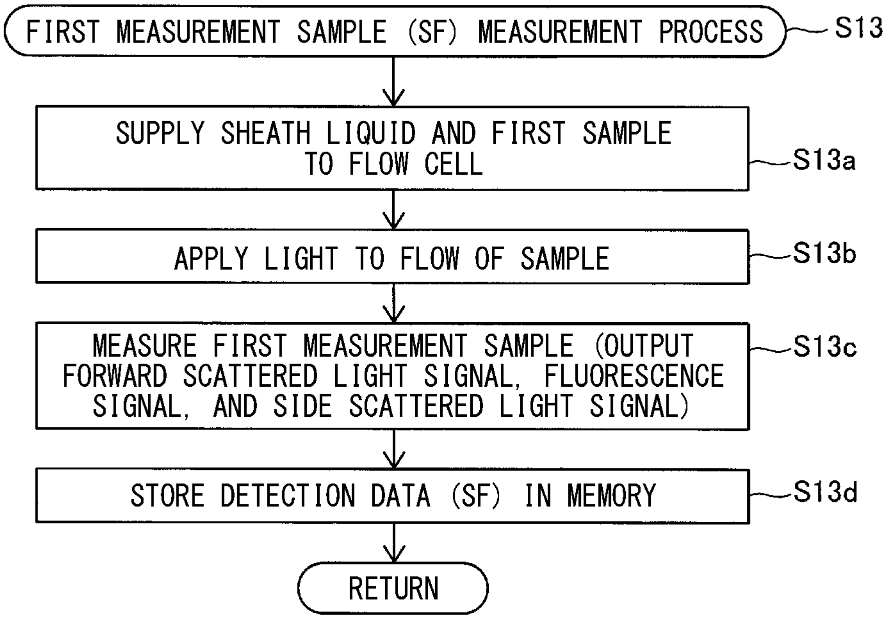
FIG. 19 is a flow chart showing a first measurement sample measuring process in FIG. 17.

In step S13*a* in FIG. 19, the microcomputer 51 operates to supply, together with a sheath liquid, the first measurement sample from the first mixing unit 41*a* to the flow cell 31. The microcomputer 51 operates to drive a not-illustrated compressor to send the sheath liquid to the flow cell 31. In a state where the sheath liquid is supplied to the flow cell 31, the microcomputer 51 operates to drive a not-illustrated compressor to supply the first measurement sample from the first mixing unit 41*a* to the flow cell 31. Thus, in the flow cell 31, the sample flow of the first measurement sample surrounded by the sheath liquid is formed.

In step S13*b*, the microcomputer 51 controls the detector 30 so as to apply laser beams to the flow of the sample formed in the flow cell 31, from the light source 32. Each time a particle passes through a beam spot formed in the flow cell 31, forward scattered light, fluorescence, and side scattered light are generated. In step S13*c*, the forward scattered light, the fluorescence, and a part of the side scattered light, and the other part of the side scattered light that has passed through the polarizing filter 36 are received by the light receivers 33*a*, 33*b*, 33*c*, and 33*d*, respectively. Light incident on each of the light receivers 33*a*, 33*b*, 33*c*, and 33*d* is converted to an electric signal, whereby FSC, FL, SSC, and DSS are outputted by the light receivers 33*a*, 33*b*, 33*c*, and 33*d*, respectively. The outputted FSC, FL, SSC, DSS are amplified by the amplification circuit 50*a*. FL becomes FLL and FLH according to an amplification factor being different The FSC, FLH, FLL, SSC, and DSS obtained through amplification by the amplification circuit 50*a* are subjected to a filtering process by the filter circuit 50*b*, are thereafter converted to digital signals by the A/D converter 50*c*, and are subjected to signal processing by the digital signal processing circuit 50*d*. Thus, the feature parameters including signal data of the forward scattered light signal (FSC), the side scattered light signal (high sensitivity) (SSH), the side scattered light signal (low sensitivity) (SSL), the high sensitivity fluorescence signal (FLH), the low sensitivity fluorescence signal (FLL), the depolarization side scattered light signal (DSS), and the like, and the feature quantities (the peak intensity P, the pulse width W, the pulse area A) for each signal data are extracted for each particle having passed through the flow cell 31. As a result, in step S13*d*, the detection data (SF) including the feature parameters for each particle is stored in the memory 50*e*, and the first measurement sample (SF) measurement process ends.

<Second Measurement Sample (CR) Measurement Process>

The second measurement sample (CR) measurement process in step S14 shown in FIG. 17 will be described. The second measurement sample (CR) measurement process is performed by the microcomputer 51 of the measurement unit 10. In the following description, each unit of the urine specimen analyzer 100 is shown in FIG. 1 to FIG. 5.

Figure 20:
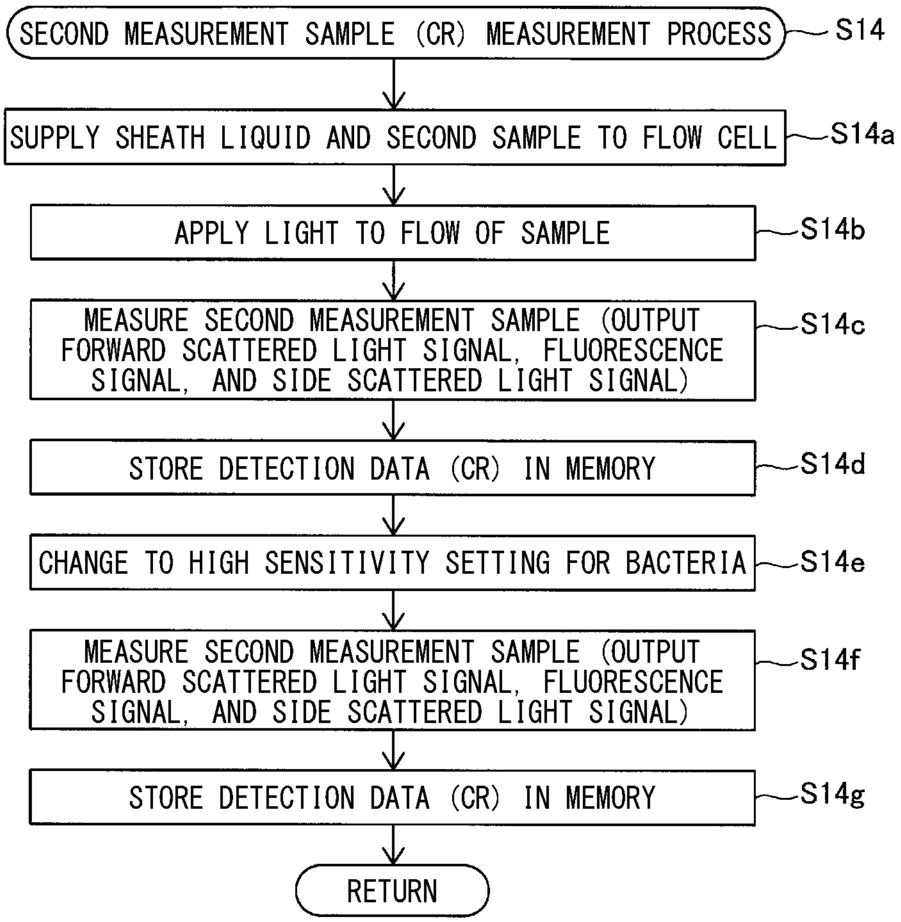
FIG. 20 is a flow chart showing a second measurement sample measuring process in FIG. 17.

In step S14*a* in FIG. 20, the microcomputer 51 operates to supply, together with a sheath liquid, the second measurement sample from the second mixing unit 41*b* to the flow cell 31. The microcomputer 51 operates to drive a not-illustrated compressor to send the sheath liquid to the flow cell 31. In a state where the sheath liquid is supplied to the flow cell 31, the microcomputer 51 operates to drive a not-illustrated compressor to supply the second measurement sample from the second mixing unit 41*b* to the flow cell 31. Thus, in the flow cell 31, the sample flow of the second measurement sample surrounded by the sheath liquid is formed.

In step S14*b*, the microcomputer 51 controls the light source 32 of the detector 30 so as to apply laser beams to the flow of the sample formed in the flow cell 31, from the light source 32. Each time a particle passes through a beam spot formed in the flow cell 31, forward scattered light, fluorescence, and side scattered light are generated. In step S14*c*, the forward scattered light, the fluorescence, and a part of the side scattered light, and the other part of the side scattered light that has passed through the polarizing filter 36 are received by the light receivers 33*a* to 33*d*, respectively. In step S14*c*, the microcomputer 51 operates the light receiver 33*b* for fluorescence at the normal sensitivity. Light incident on each of the light receivers 33*a* to 33*d* is converted to an electric signal, whereby FSC, FL (normal sensitivity), SSC, and DSS are outputted by the light receivers 33*a* to 33*d*, respectively. The outputted FSC, FL, SSC, and DSS are amplified by the amplification circuit 50*a*. FL (normal sensitivity) becomes FLL and FLH according to an amplification factor being different.

The FSC, FLH, FLL, SSC, and DSS obtained through amplification by the amplification circuit 50*a* are subjected to a filtering process by the filter circuit 50*b*, are thereafter converted to digital signals by the A/D converter 50*c*, and are subjected to signal processing by the digital signal processing circuit 50*d*. Thus, the feature parameters including signal data of the forward scattered light signal (FSC), the side scattered light signal (high sensitivity) (SSH), the side scattered light signal (low sensitivity) (SSL), the high sensitivity fluorescence signal (FLH), the low sensitivity fluorescence signal (FLL), the depolarization side scattered light signal (DSS), and the like, and the feature quantities (the peak intensity P, the pulse width W, the pulse area A) for each signal data are extracted for each particle having passed through the flow cell 31. As a result, in step S14*d*, the detection data (CR) including the feature parameters for each particle is stored in the memory 50*e*.

In steps S14*e* to S14*g*, the light receiver 33*b* is operated with high sensitivity setting for measuring bacteria to collect bacteria detection data. In step S14*e*, when a predetermined time has elapsed from start of supply of the second measurement sample to the flow cell 31, the microcomputer 51 changes the sensitivity of the light receiver 33*b* to the high sensitivity setting for measuring bacteria.

In step S14*f*, the microcomputer 51 causes the measurement unit 10 to measure the second measurement sample in a state where sensitivity of the light receiver 33*b* is set as high sensitivity setting for measuring bacteria. The measurement operation is similar to that in step S14*c* described above. Thus, FL(B) is outputted from the light receiver 33*b* at high sensitivity for measuring bacteria, and signals (FSC, SSC, DSS) at the same sensitivity setting as in step S14*c* are outputted from the other light receivers 33*a*, 33*c*, and 33*d*, respectively. Each of FSC, FL(B), SSC, and DSS signals is amplified by the amplification circuit 50*a*. FL(B) outputted from the light receiver 33*b* at high sensitivity is amplified at the same amplification factor as the high amplification factor by the amplification circuit 50*a*, and a high sensitivity fluorescence signal (FLH(B)) is obtained.

The FSC, FLH(B), SSH, SSL, and DSS obtained through the amplification are subjected to a filtering process by the filter circuit 50*b*, are thereafter converted to digital signals by the A/D converter 50*c*, and are subjected to predetermined signal processing by the digital signal processing circuit 50*d*. As the feature parameter, FLH(B)P is extracted from FLH(B), and FSCP is extracted from FSC through the signal processing. In step S14*g*, data of the feature parameters extracted for each particle, are stored as the detection data (CR) in the memory 50*e*. When the above-described process has been completed, the microcomputer 51 returns the process to the main routine.

The count information for each kind of urine particle is obtained, by the processor 21, from the detection data (SF) of the first measurement sample and the detection data (CR) of the second measurement sample, which are obtained as described above, based on a combination of two or more preset feature parameters, in step S4 (see FIG. 17).

(Determination as to Suspicion of *Trichomonas* Infection)

Next, determination as to *Trichomonas* infection based on the count information of *Trichomonas vaginalis* and the information as shown in step S7 in FIG. 17 will be described in detail. The determination as to *Trichomonas* infection is performed by the processor 21 of the analysis unit 20. In an example shown in FIG. 21, the process is performed in the order of the determination rule 2, the determination rule 1, and the determination rule 3. In the following description, each unit of the urine specimen analyzer 100 is shown in FIG. 1 to FIG. 5, FIG. 13, and FIG. 15.

In step S7*a*, the processor 21 performs determination based on the determination rule 2. That is, the processor 21 determines whether or not all of the criteria (4) Ywbc<N4, (5) Zrbc<N5, (6) Zbact<N6, and (7) Zylc<N7 are satisfied.

In a case where all of the criteria (4) to (7) are satisfied, the processor 21 advances the process to step S7*b*. In a case where one or more of the criteria (4) to (7) is not satisfied, the processor 21 advances the process to step S7*e*, generates a flag indicating "negative or non-determinable" about suspicion of *Trichomonas* infection, and causes the storage unit 22 to store the flag.

In step S7*b*, the processor 21 performs determination based on the determination rule 1. That is, the processor 21 determines whether or not all of the criteria (1) Xsf>N1, (2) Xcr>N2, and (3) Ysec>N3 are satisfied. As the threshold values N1 to N3, values of the threshold value set having been set in step S6 as described above are used.

In a case where all of the criteria (1) to (3) are satisfied, the processor 21 advances the process to step S7*c*. In a case where one or more of the criteria (1) to (3) is not satisfied, the processor 21 advances the process to step S7*e*, generates a flag indicating "negative or non-determinable" about suspicion of *Trichomonas* infection, and causes the storage unit 22 to store the flag.

In step S7*c*, the processor 21 performs determination based on the determination rule 3. That is, the processor 21 determines whether or not the criterion (8) Ztrich>N8 is satisfied.

In a case where the criterion (8) is satisfied, the processor 21 advances the process to step S7*d*. In a case where the criterion (8) is not satisfied, the processor 21 advances the process to step S7*e*, generates a flag indicating "negative or non-determinable" about suspicion of *Trichomonas* infection, and causes the storage unit 22 to store the flag.

In step S7*d*, the processor 21 generates a positive-indicating flag indicating that *Trichomonas* infection "is suspected", and causes the storage unit 22 to store the flag.

When the positive-indicating flag is stored in the storage unit 22 in step S7*d* or the flag indicating "negative or non-determinable" is stored in the storage unit 22 in step S7*e*, the processor 21 returns the process to the main routine. In the example shown in FIG. 21, the determination is performed in the order of the determination rule 2, the determination rule 1, and the determination rule 3. However, the order for the determination rule 2, the determination rule 1, and the determination rule 3 is discretionary in the determination. The determination rule 1 may be firstly executed or the determination rule 3 may be firstly executed. The order of the determination rules does not change the determination result.

(Process of Outputting Information about Suspicion of *Trichomonas* Infection)

Figure 22:
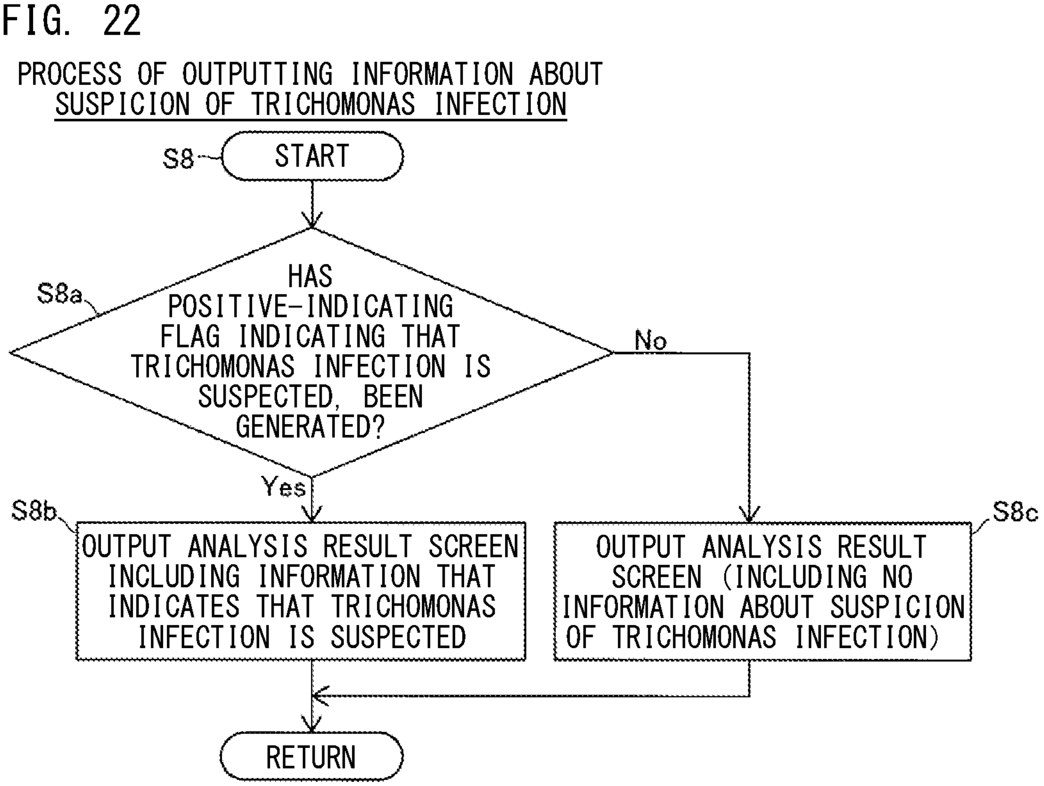
FIG. 22 is a flow chart showing a process, in FIG. 17, of outputting information about suspicion of *Trichomonas* infection.

Next, a process of outputting information about suspicion of *Trichomonas* infection as shown in step S8 in FIG. 17 will be described in detail with reference to FIG. 22. The process of outputting information about suspicion of *Trichomonas* infection is performed by the processor 21 of the analysis unit 20.

In step S8*a*, the processor 21 determines whether or not the positive-indicating flag about suspicion of *Trichomonas* infection is stored in the storage unit 22 as a result of the most recent detection of the urine specimen 5. That is, in a case where the positive-indicating flag is generated and stored in the storage unit 22 in step S7*d* in the determination shown in FIG. 21 (Yes in step S8*a*), the processor 21 advances the process to step S8*b*. Meanwhile, in a case where the flag indicating "negative or non-determinable" is generated and stored in the storage unit 22 in step S7*e* in the determination shown in FIG. 21 (No in step S8*a*), the processor 21 advances the process to step S8*c*.

In step S8*b*, the processor 21 outputs the analysis result screen 81 (see FIG. 16) to the display unit 20*c*. The processor 21 generates the analysis result screen 81 including both the count information generated for each kind of urine particle in step S4, and the information 80 about suspicion of *Trichomonas* infection, and outputs the analysis result screen 81 to the display unit 20*c*. As shown in FIG. 16, as a result, information ("Trich" as analysis item and "*Trichomonas*?" indicating that *Trichomonas* infection is suspected) indicating that *Trichomonas* infection is suspected is displayed in the information display column 83 of the analysis result screen 81.

In step S8*c*, the processor 21 outputs the analysis result screen 81 to the display unit 20*c*. The processor 21 generates the analysis result screen 81 that includes the count information generated for each kind of the urine particles in step S4 and does not include the information 80 about suspicion of *Trichomonas* infection, and outputs the analysis result screen 81 to the display unit 20*c*. Therefore, on the analysis result screen 81 outputted in step S8*c*, the information about suspicion of *Trichomonas* infection is not displayed in the information display column 83 unlike in the display manner shown in FIG. 16.

As described above, a urine specimen analysis method according to the first embodiment includes (S5) obtaining the count information 70 about the number of *Trichomonas vaginalis* cells and the first information 71 including the count information about at least one of the number of squamous epithelium cells and the number of white blood cells, based on the detection data of the urine particles in the urine specimen 5. Even at the early stage of *Trichomonas* infection, both the number of *Trichomonas vaginalis* cells and the numbers of squamous epithelium cells and white blood cells appearing in the urine specimen 5 of a patient who suffers from *Trichomonas* infection are significantly increased. Therefore, in a case where the value of the count information obtained as the first information 71 is high, reliability of the count information 70 about the number of *Trichomonas vaginalis* cells can be determined to be high. Meanwhile, in a case where the value of the count information obtained as the first information 71 is low, reliability of the count information 70 about the number of *Trichomonas vaginalis* cells can be determined to be low. Accordingly, the urine specimen analysis method according to the first embodiment includes outputting the information 80 about suspicion of *Trichomonas* infection based on at least the count information 70 about the number of *Trichomonas vaginalis* cells and the first information 71 (S7 and S8). Thus, reliability of the count information 70 about the number of *Trichomonas vaginalis* cells can be enhanced, based on the first information 71 serving as an index of reliability of the count information 70 about the number of *Trichomonas vaginalis* cells, according to even the detection data of the urine specimen 5 in which, in addition to *Trichomonas vaginalis*, another urine particle having a feature, in form, similar to that of *Trichomonas vaginalis* is likely to be mixed. As a result, also in a case where the number of urine particles identified as *Trichomonas vaginalis* is small in the urine specimen 5, accurate determination as to suspicion of *Trichomonas* infection can be performed based on the count information 70 about the number of *Trichomonas vaginalis* cells and the first information 71. That is, even at the early stage of *Trichomonas* infection, accurate determination as to suspicion of *Trichomonas* infection can be performed.

Other Embodiments

Next, other embodiments different from the first embodiment described above will be described.

In the first embodiment described above, for example, the information 80 about suspicion of *Trichomonas* infection is outputted by using the three determination rules. However, the present disclosure is not limited thereto, and the three determination rules may not necessarily be used. An embodiment of a method for performing determination as to suspicion of *Trichomonas* infection will be described below.

Second Embodiment

Figure 21:
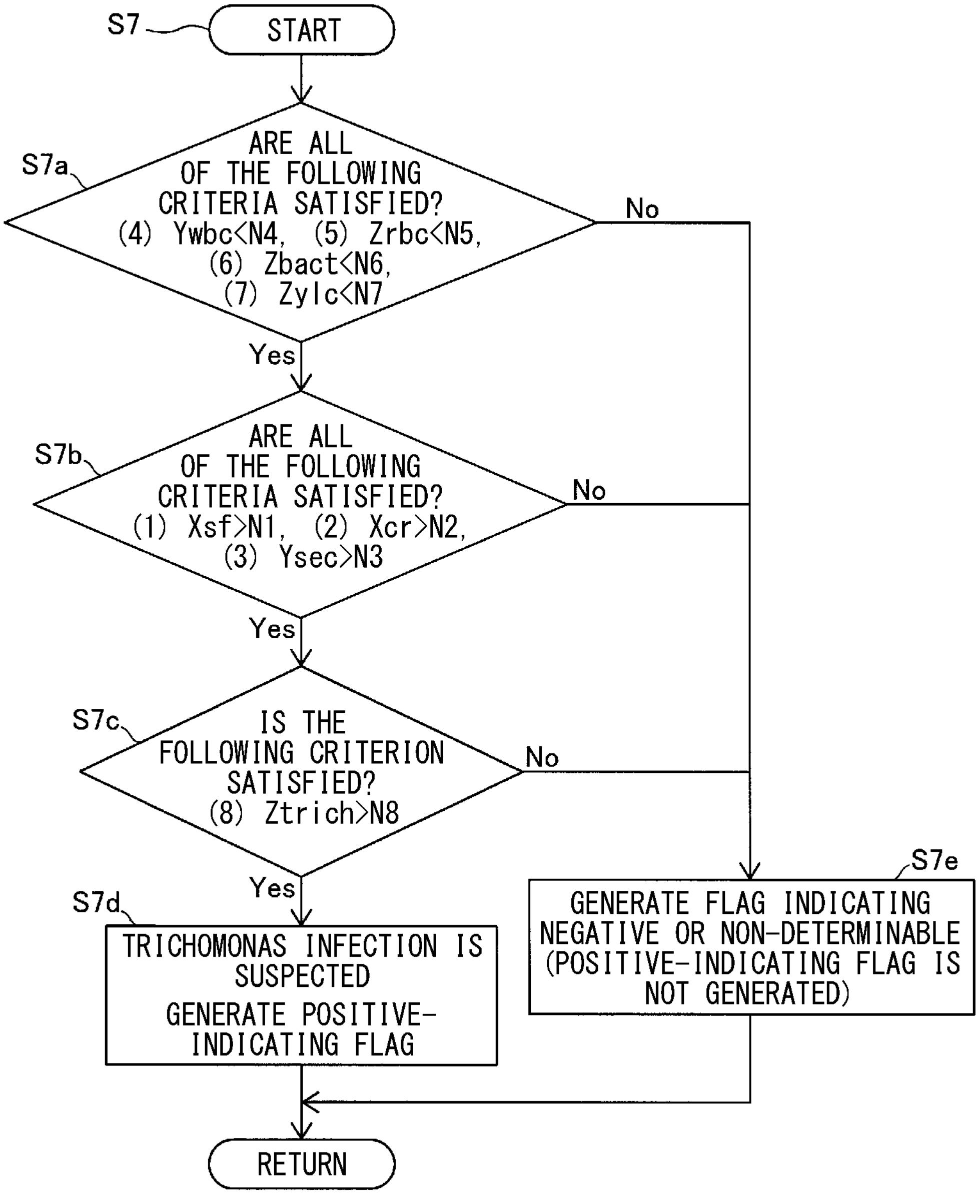
FIG. 21 is a flow chart showing a determination process, in FIG. 17, based on count information of *Trichomonas vaginalis* cells, first information, and second information.
Figure 23:
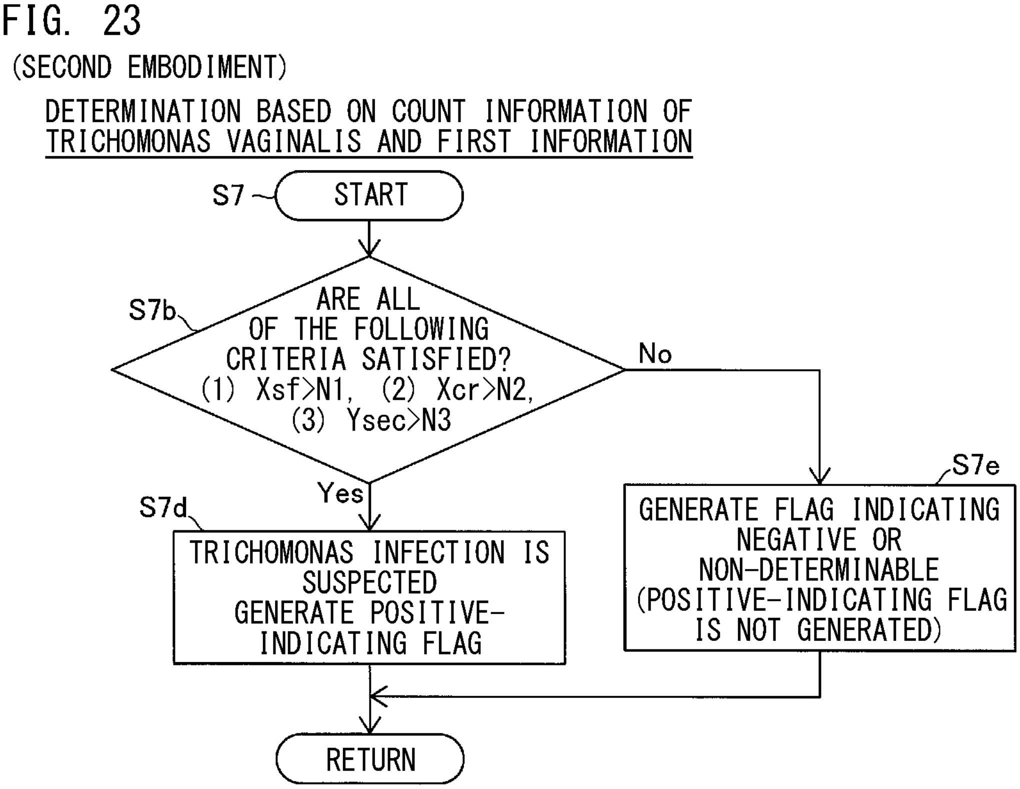
FIG. 23 is a flow chart showing a determination process based on count information of *Trichomonas vaginalis* cells and the first information, according to a second embodiment.

FIG. 23 shows a specific example of a process of performing determination as to suspicion of *Trichomonas* infection as shown in step S7 in FIG. 17, and shows a second embodiment performed instead of the flow (S7*a* to S7*e*) of the first embodiment shown in FIG. 21. In the second embodiment, determination as to suspicion of *Trichomonas* infection is performed only by step S7*b* corresponding to the determination rule 1.

In step S7*b*, the processor 21 performs the determination based on the determination rule 1. That is, the processor 21 determines whether or not all of the following criteria (1) to (3) are satisfied.

(1) Xsf>N1, (2) Xcr>N2, (3) Ysec>N3

In a case where all of the criteria (1) to (3) are satisfied, the processor 21 advances the process to step S7*d*. In a case where one or more of the criteria (1) to (3) is not satisfied, the processor 21 advances the process to step S7*e*, generates a flag indicating "negative or non-determinable" about suspicion of *Trichomonas* infection, and causes the storage unit 22 to store the flag.

In step S7*d*, the processor 21 generates a positive-indicating flag indicating that *Trichomonas* infection "is suspected" and causes the storage unit 22 to store the flag. In a case where the positive-indicating flag is stored in the storage unit 22 in step S7*d*, or the flag indicating "negative or non-determinable" is stored in the storage unit 22 in step S7*e*, the processor 21 returns the process to the main routine.

As in the second embodiment, in the present disclosure, the information 80 about suspicion of *Trichomonas* infection can be outputted based on at least the count information 70 about the number of *Trichomonas vaginalis* cells and the first information 71, without obtaining and analyzing the second information 72.

Third Embodiment

Figure 24:
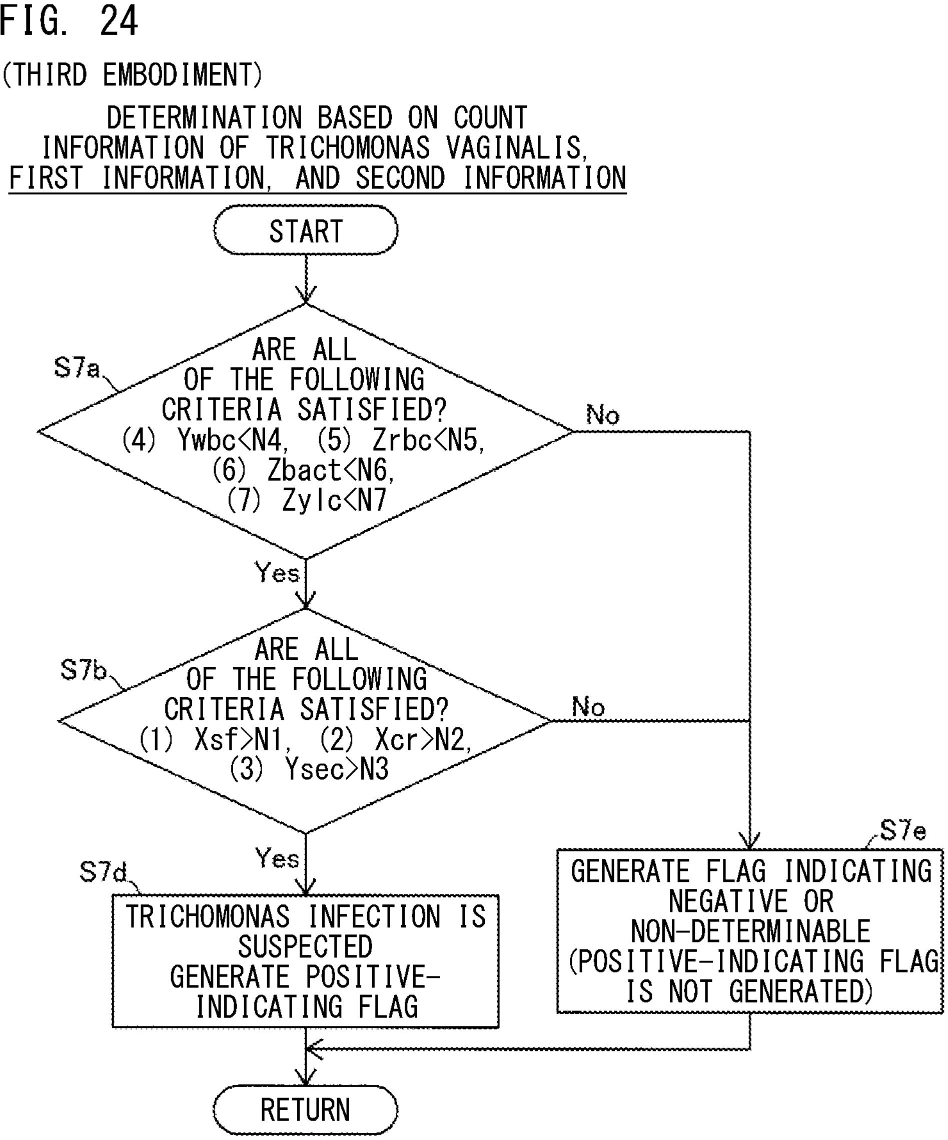
FIG. 24 is a flow chart showing a determination process based on count information of *Trichomonas vaginalis* cells, the first information, and the second information, according to a third embodiment.

FIG. 24 shows a specific example of a process of performing determination as to suspicion of *Trichomonas* infection as shown in step S7 in FIG. 17, and shows a third embodiment performed instead of the flow (S7*a* to S7*e*) of the first embodiment shown in FIG. 21. In the third embodiment, determination as to suspicion of *Trichomonas* infection is performed by two steps, that is, step S7*b* corresponding to the determination rule 1 and step S7*a* corresponding to the determination rule 2.

In step S7*a*, the processor 21 performs the determination based on the determination rule 2. That is, the processor 21 determines whether or not all of the criteria (4) Ywbc<N4, (5) Zrbc<N5, (6) Zbact<N6, and (7) Zylc<N7 are satisfied.

In a case where all of the criteria (4) to (7) are satisfied, the processor 21 advances the process to step S7*b*. In a case where one or more of the criteria (4) to (7) is not satisfied, the processor 21 advances the process to step S7*e*, generates a flag indicating "negative or non-determinable" about suspicion of *Trichomonas* infection, and causes the storage unit 22 to store the flag.

In step S7*b*, the processor 21 performs the determination based on the determination rule 1. That is, the processor 21 determines whether or not all of the criteria (1) Xsf>N1, (2) Xcr>N2, and (3) Ysec>N3 are satisfied.

In a case where all of the criteria (1) to (3) are satisfied, the processor 21 advances the process to step S7*d*. In a case where one or more of the criteria (1) to (3) is not satisfied, the processor 21 advances the process to step S7*e*, generates a flag indicating "negative or non-determinable" about suspicion of *Trichomonas* infection, and causes the storage unit 22 to store the flag.

In step S7*d*, the processor 21 generates a positive-indicating flag indicating that *Trichomonas* infection "is suspected" and causes the storage unit 22 to store the flag. In a case where the positive-indicating flag is stored in the storage unit 22 in step S7*d*, or the flag indicating "negative or non-determinable" is stored in the storage unit 22 in step S7*e*, the processor 21 returns the process to the main routine.

Fourth Embodiment

Figure 25:
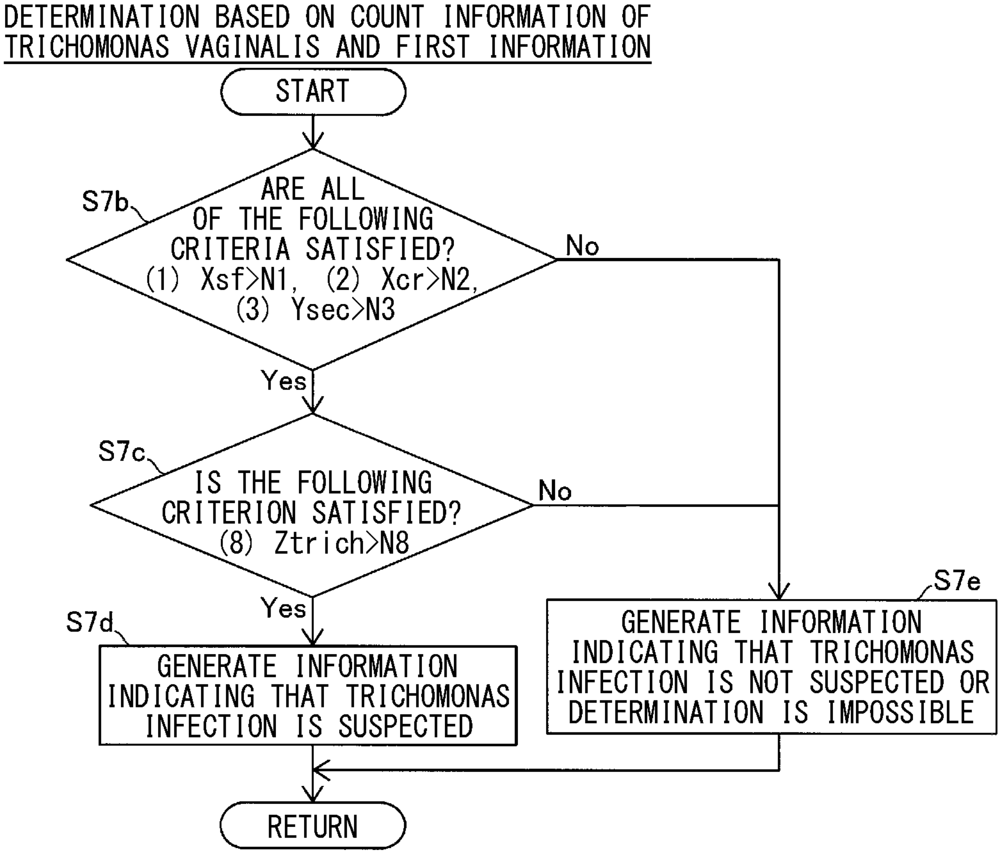
FIG. 25 is a flow chart showing a determination process based on count information of *Trichomonas vaginalis* cells and first information, according to a fourth embodiment.

FIG. 25 shows a specific example of a process of performing determination as to suspicion of *Trichomonas* infection as shown in step S7 in FIG. 17, and shows a fourth embodiment performed instead of the flow (S7*a* to S7*e*) of the first embodiment shown in FIG. 21. In the fourth embodiment, determination as to suspicion of *Trichomonas* infection is performed by step S7*b* corresponding to the determination rule 1 and step S7*c* corresponding to the determination rule 3.

In step S7*b*, the processor 21 performs the determination based on the determination rule 1. That is, the processor 21 determines whether or not all of the criteria (1) Xsf>N1, (2) Xcr>N2, and (3) Ysec>N3 are satisfied.

In a case where all of the criteria (1) to (3) are satisfied, the processor 21 advances the process to step S7*c*. In a case where one or more of the criteria (1) to (3) is not satisfied, the processor 21 advances the process to step S7*e*, generates a flag indicating "negative or non-determinable" about suspicion of *Trichomonas* infection, and causes the storage unit 22 to store the flag.

In step S7*c*, the processor 21 determines whether or not the criterion of (8) Ztrich>N8 is satisfied, based on the determination rule 3. In a case where the criterion (8) is satisfied, the processor 21 advances the process to step S7*d*. In a case where the criterion (8) is not satisfied, the processor 21 advances the process to step S7*e*, generates a flag indicating "negative or non-determinable" about suspicion of *Trichomonas* infection, and causes the storage unit 22 to store the flag.

In step S7*d*, the processor 21 generates a positive-indicating flag indicating that *Trichomonas* infection "is suspected" and causes the storage unit 22 to store the flag. In a case where the positive-indicating flag is stored in the storage unit 22 in step S7*d*, or the flag indicating "negative or non-determinable" is stored in the storage unit 22 in step S7*e*, the processor 21 returns the process to the main routine.

(Determination Rule 1 According to Modification)

Figure 26:
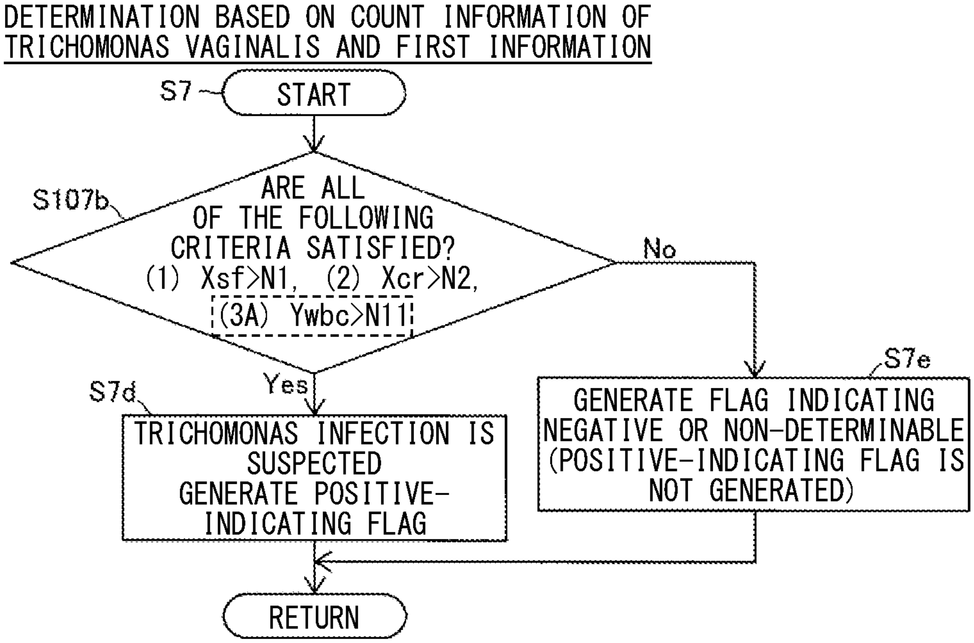
FIG. 26 is a flow chart illustrating a determination rule 1A according to a modification.

In the first embodiment described above, an example of the determination rule 1 based on the count information 70 about the number of *Trichomonas vaginalis* cells and the count information 71*a* (see FIG. 13) of squamous epithelium cells as the first information 71, is described. However, the present disclosure is not limited thereto. As shown in FIG. 26, a determination rule 1A based on the count information 71*b* of white blood cells instead of the count information 71*a* of squamous epithelium cells may be set.

The determination rule 1A includes the following criteria (1), (2), and (3A).

(1) the count value Xsf of the first count information 70*a* is greater than the threshold value N1 (Xsf>N1), (2) the count value Xcr of the second count information 70*b* is greater than the threshold value N2 (Xcr>N2), (3A) the count value Ywbc of the count information 71*b* of white blood cells is greater than a threshold value N11 (Ywbc>N11).

In a case where all of the criteria (1), (2), and (3A) in the determination rule 1A are satisfied, the analysis unit 20 determines that *Trichomonas* infection "is suspected" according to the determination rule 1A. In a case where one or more of the three criteria in the determination rule 1A is not satisfied, determination that "*Trichomonas* infection is not suspected or determination is impossible" is made according to the determination rule 1A.

Specific examples of the threshold values in the determination rule 1A are N1=1.0/μL, N2=5.0/μL, and N11=25.0/μL. Therefore, the determination criteria (1), (2), and (3) in step S7*b* shown in FIG. 21, FIG. 23, FIG. 24, and FIG. 25 may be replaced with the criteria (1), (2), and (3A) of the determination rule 1A.

For example, FIG. 26 shows an example in which step S7*b* in the determination process flow for suspicion of *Trichomonas* infection according to the second embodiment shown in FIG. 23 is replaced with step S107*b* corresponding to the determination rule 1A (see a portion surrounded by dotted lines in FIG. 26).

Furthermore, by combining the determination rule 1 and the determination rule 1A, the determination criteria (3) and (3A) for both the count information about the number of squamous epithelium cells and the count information about the number of white blood cells may be set in the determination rule 1.

EXAMPLES

Next, a result of experiments performed for verifying the effect of the present disclosure will be described.

First Example

Firstly, a result of experiments performed for verifying accuracy of determination as to suspicion of *Trichomonas* infection according to the count information 70 about the number of *Trichomonas vaginalis* cells and the first information 71 will be described.

In the experiment, analysis by the urine specimen analyzer 100 and a visual microscope examination (visual examination) were performed for the urine specimen 5 to verify determination accuracy of the analysis result. That is, a degree to which the result of determination performed by the analysis unit 20 for suspicion of *Trichomonas* infection, and the result of visual microscope examination conformed to each other was verified.

In the experiment, in example 1, the determination was performed by the analysis unit 20 by the simplest determination process (determination process according to only the determination rule 1) described in the second embodiment shown in FIG. 23, in order to verify accuracy of determination according to the count information 70 about the number of *Trichomonas vaginalis* cells and the first information 71. That is, in example 1, only the determination rule 1 based on the above-described criteria (1), (2), and (3) in which the first count information 70*a*, the second count information 70*b*, and the count information of squamous epithelium cells were used, was executed. For the determination, the threshold value set 75*a* shown in FIG. 15 was used.

In example 2, the determination was performed by the analysis unit 20 by the determination process (determination process according to only the determination rule 1A) according to the modification shown in FIG. 26. That is, in example 2, the determination rule 1A based on the above-described criteria (1), (2), and (3A) in which the first count information 70*a*, the second count information 70*b*, and the count information of white blood cells were used, was executed.

In a comparative example, the determination was performed by the analysis unit 20 according to only the count information 70 about the number of *Trichomonas vaginalis* cells. That is, the comparative example was the determination process according to only the criteria (1) and (2) in the determination rule 1. The threshold values N1 and N2 in the criteria (1) and (2) were the same among example 1, example 2, and the comparative example.

In example 1 and the comparative example, the experiment was performed for a group of the same 1200 urine specimens. In example 2, the experiment was performed separately from example 1 and the comparative example, for a group of 1234 urine specimens. The specimen population was the same between example 1 and the comparative example. In example 2, the specimen population was likely to be different from that of example 1 and the comparative example.

Table 1 indicates the result of the experiment in example 1.

TABLE 1

[Example 1] Analysis result according to Trichomonas count information and first auxiliary information (squamous epithelium cell)

| | | Visual examination | | |
|---|---|---|---|---|
| | | Positive | Negative | Total |
| Analysis result | Positive | 23 | 78 | 101 |
| | Negative | 8 | 1091 | 1099 |
| | Total | 31 | 1169 | 1200 |
| Sensitivity | | Specificity | Positive hit rate | |
| 74.2% | | 93.3% | 22.8% | |

The analysis result in example 1 indicates that the sensitivity was 74.2%, the specificity was 93.3%, and the positive hit rate was 22.8%, relative to the visual examination.

Table 2 indicates the result of the experiment in example 2.

TABLE 2

[Example 2] Analysis result according to Trichomonas count information and first auxiliary information (white blood cell)

| | | Visual examination | | |
|---|---|---|---|---|
| | | Positive | Negative | Total |
| Analysis result | Positive | 25 | 106 | 131 |
| | Negative | 9 | 1094 | 1103 |
| | Total | 34 | 1200 | 1234 |
| Sensitivity | | Specificity | Positive hit rate | |
| 73.5% | | 91.2% | 19.1% | |

The analysis result in example 2 indicates that the sensitivity was 73.5%, the specificity was 91.2%, and the positive hit rate was 19.1%, relative to the visual examination.

Table 3 indicates the result of the experiment in the comparative example.

TABLE 3

[Comparative example] Analysis result according to only Trichomonas count information (using no auxiliary information)

| | | Visual examination | | |
|---|---|---|---|---|
| | | Positive | Negative | Total |
| Analysis result | Positive | 25 | 169 | 194 |
| | Negative | 6 | 1000 | 1006 |
| | Total | 31 | 1169 | 1200 |
| Sensitivity | | Specificity | Positive hit rate | |
| 80.6% | | 85.5% | 12.9% | |

The analysis result in the comparative example indicates that the sensitivity was 80.6%, the specificity was 85.5%, and the positive hit rate was 12.9%, relative to the visual examination.

As described above, in example 1 and example 2 in which the first information 71 including the count information of squamous epithelium cells or white blood cells was taken into consideration, it was confirmed that the specificity was enhanced, and false-positive determination was able to be substantially reduced as compared with the comparative example. That is, although the number of false positive specimens was 169 in the comparative example, the number of false-positive specimens was reduced to 78 in example 1 and the number of false-positive specimens was reduced to 106 in example 2. Thus, the effect of the present disclosure that the determination accuracy can be enhanced by adding the first information 71 (whether or not squamous epithelium cells or white blood cells appear in urine) to the determination criterion about suspicion of *Trichomonas* infection, was verified.

Second Example

Next, a comparative experiment for the analysis results according to the three modes shown in FIG. 15 will be described. That is, the determination results about suspicion of *Trichomonas* infection according to three modes having different threshold value settings were compared.

In the experiment, similarly to the above-described first example, analysis by the urine specimen analyzer 100 and visual microscope examination (visual examination) were performed for the urine specimen 5 to verify the determination accuracy of the analysis result. That is, a degree to which the result of determination performed by the analysis unit 20 for suspicion of *Trichomonas* infection and the result of the visual microscope examination conformed to each other, was verified.

In example 3, the determination as to suspicion of *Trichomonas* infection was performed according to the first mode (standard setting).

In example 4, the determination as to suspicion of *Trichomonas* infection was performed according to the second mode (sensitivity-oriented setting).

In example 5, the determination as to suspicion of *Trichomonas* infection was performed according to the third mode (specificity-oriented setting).

The number of the urine specimens 5 used in the experiment was 1232. For the same urine specimen group, the experiment of each of examples 3 to 5 was performed. In examples 3 to 5, as shown in FIG. 23, only the determination rule 1 based on the above-described criteria (1), (2), and (3) in which the first count information 70*a*, the second count information 70*b*, and the count information of squamous epithelium cells were used, was executed.

Table 4 indicates experiment results in example 3.

TABLE 4

[Example 3] Detection performance according to the first mode (standard setting)

| | | Visual examination | | |
|---|---|---|---|---|
| | | Positive | Negative | Total |
| Analysis result | Positive | 17 | 4 | 21 |
| | Negative | 17 | 1194 | 1211 |
| | Total | 34 | 1198 | 1232 |
| Sensitivity | | Specificity | Positive hit rate | |
| 50.0% | | 99.7% | 81.0% | |

Table 5 indicates experiment results in example 4.

TABLE 5

[Example 4] Detection performance according to the second mode (sensitivity-oriented setting)

| | | Visual examination | | |
|---|---|---|---|---|
| | | Positive | Negative | Total |
| Analysis result | Positive | 26 | 114 | 140 |
| | Negative | 8 | 1084 | 1092 |
| | Total | 34 | 1198 | 1232 |
| Sensitivity | | Specificity | Positive hit rate | |
| 76.5% | | 90.5% | 18.6% | |

Table 6 indicates experiment results in example 5.

TABLE 6

[Example 5] Detection performance according to the third mode (specificity-oriented setting)

| | | Visual examination | | |
|---|---|---|---|---|
| | | Positive | Negative | Total |
| Analysis result | Positive | 7 | 0 | 7 |
| | Negative | 27 | 1198 | 1225 |
| | Total | 34 | 1198 | 1232 |
| Sensitivity | | Specificity | Positive hit rate | |
| 20.6% | | 100.0% | 100.0% | |

According to Table 4 to Table 6, it has been confirmed that information useful particularly for a user for whom early detection is important can be provided with higher sensitivity in the second mode (sensitivity-oriented setting) as compared with the first mode (standard setting). It has been confirmed that information useful particularly for a user for whom certainty is important even at an early stage of *Trichomonas* infection can be provided with higher specificity in the third mode (specificity-oriented setting), as compared with the first mode (standard setting). It has been confirmed that information in which sensitivity and specificity are well-balanced can be provided particularly for the purpose of early detection of *Trichomonas* infection since, in the first mode (standard setting), specificity is higher than that in the second mode, and sensitivity is higher than that in the third mode.

(Modification)

The embodiments disclosed herein are illustrative in all aspects and should not be construed as being restrictive. The scope of the present invention is defined not by the description of the above embodiments but by the scope of the claims, and includes meaning equivalent to the scope of the claims and all modifications within the scope.

In the above-described first embodiment, an example in which the detector 30 is implemented by a flow cytometer is described. However, the present disclosure is not limited thereto. For example, the detector 30 may be configured as a photographing device for taking a microscope image of a urine particle in a measurement sample in which the urine particle is stained by mixing a urine specimen and a reagent. In this case, a urine particle can be identified for each kind based on the feature in form and a stained state (stained portion, coloring, and the like) of the urine particle in the image taken by the detector 30, to obtain the count information. The detector 30 configured as a photographing device may take an image of a urine particle in a sample that is stationary in a sample container for photographing or may continuously take an image of a urine particle in the flow of the sample flowing in a flow cell.

In the above-described first embodiment, an example in which selection from three modes, that is, the first mode, the second mode, and the third mode, having different threshold value sets can be received, is described. However, the present disclosure is not limited thereto. One threshold value set may be merely set without receiving selection of a mode. For example, the threshold value set in the determination rule 1 may be only an unchangeable threshold value set of the first mode. In a case where selection of a mode can be received, the number of the selectable modes is not limited to three, and may be two or greater than or equal to four.

In the above-described first embodiment, an example in which the measurement unit 10 of the urine specimen analyzer 100 includes the specimen transportation unit 12, the sample preparation unit 40, and the specimen distributing unit 45, is described. However, the present disclosure is not limited thereto. The measurement unit 10 may not necessarily include the specimen transportation unit 12, the sample preparation unit 40, and the specimen distributing unit 45. In this case, a measurement sample prepared in advance is obtained, and the measurement sample may be supplied to the detector 30 of the measurement unit 10.

What is claimed is:

1. A urine specimen analyzer comprising:

a transportation unit configured to transport a rack holding containers each storing a urine specimen, thereby positioning each of the urine specimens at a suction position;

a suction unit configured to suction the urine specimen at the suction position;

a mixing unit configured to mix the urine specimen and a staining reagent;

a flow cytometry-based detector configured to detect a urine particle in the urine specimen, the detector including: a flow cell through which the urine specimen flows; a light source configured to apply light to the flow cell; and a light receiver configured to sense fluorescence and scattered light from the urine particle; and an analysis unit configured to analyze the urine particles by:

plotting the urine particles in a coordinate space, the urine particles being plotted at coordinates corresponding to a plurality of feature parameters of the individual urine particles obtainable from the fluorescence and scattered light sensed by the light receiver, wherein the plots of the individual urine particles form clusters of different types;

counting red blood cell (RBC), white blood cell (WBC), epithelial cell (EC), bacterium (BACT) and cast (CAST) based on numbers of the plots in the respective clusters;

providing an analysis report including the counts of the types of the urine particles;

wherein the analysis unit is further configured to count a number of *Trichomonas vaginalis* cells by counting plots in a predetermined area of the coordinate space, and the analysis unit is configured to identify an infection-suspected urine specimen among the urine specimens, the infection-suspected urine specimen containing (i) *Trichomonas vaginalis* cells at a number greater than a first threshold value; and (ii) white blood cells and/or epithelial cells at a number greater than a second threshold value, wherein the second threshold value is greater than or equal to the first threshold value, and wherein the analysis unit is configured to present a *Trichomonas* infection flag in the analysis report of the identified urine specimen.

2. The urine specimen analyzer of claim 1, wherein the analysis unit is configured to identify the infection-suspected urine specimen that further contains at least one of:

(iii) the *Trichomonas vaginalis* cells at a number counted from the urine specimen mixed with a first reagent, greater than a third threshold value; and/or (iv) the *Trichomonas vaginalis* cells at a number, counted from the urine specimen mixed with a second reagent, greater than a fourth threshold value.

3. The urine specimen analyzer of claim 1, wherein the analysis unit is configured to obtain further information about a type of urine particle different from the white blood cells and/or epithelial cells based on a distribution of plots in the predetermined area of the coordinate space; and present the *Trichomonas* infection flag in the analysis report of the identified urine specimen further based on the further information.

4. The urine specimen analyzer of claim 3, wherein the further information is used to inhibit a false-positive determination of the *Trichomonas* infection flag.

5. The urine specimen analyzer of claim 1, wherein the mixing unit includes a first mixing unit configured to mix the urine specimen and a first reagent, and a second mixing unit configured to mix the urine specimen and a second reagent, and the detector configured to detect each of a urine particle in the urine specimen in which the first reagent is mixed, and a urine particle in the urine specimen in which the second reagent is mixed.

6. The urine specimen analyzer of claim 1, wherein the analysis unit is configured to:

receive selection of an analysis mode from a plurality of modes including a first mode and a second mode;

apply a first set of the first threshold value and the second threshold value in response to the selection of the first mode, and apply a second set of the first threshold value and the second threshold value, the second set being different from the first set, in response to the selection of the second mode.

* * * * *